United States Patent [19]

Hosoda et al.

[11] Patent Number: 5,427,917
[45] Date of Patent: Jun. 27, 1995

[54] METHOD OF DETERMINING HUMAN ACID GLUTATHIONE S-TRANSFERASE, REAGENT, THEREFOR, KIT THEREFOR, METHOD OF DIAGNOSING CANCER IN DIGESTIVE ORGANS, AND MONOCLONAL ANTIBODY FOR USE THEREIN

[75] Inventors: Kenji Hosoda, Saitama; Hitomi Honda; Takaharu Kubota, both of Hino; Hideaki Suzuki, Koganei, all of Japan

[73] Assignee: Teijin Limited, Osaka, Japan

[21] Appl. No.: 169,963

[22] Filed: Dec. 20, 1993

Related U.S. Application Data

[63] Continuation of Ser. No. 731,367, Jul. 16, 1991, abandoned, which is a continuation-in-part of Ser. No. 304,648, Feb. 1, 1989, abandoned.

[30] Foreign Application Priority Data

Feb. 1, 1988 [JP] Japan ................................. 63-19602
Oct. 26, 1988 [JP] Japan ................................ 63-268292
Nov. 10, 1988 [JP] Japan ................................ 63-282546

[51] Int. Cl.⁶ ........................................... G01N 33/53
[52] U.S. Cl. ..................... 435/7.4; 435/7.92; 435/7.94; 435/15; 436/64; 436/518; 436/548
[58] Field of Search .............. 435/7.1, 7.4, 7.92, 435/7.94, 15, 250.27, 810; 436/518, 548, 808, 64; 935/96, 110; 530/350, 387, 806; 424/85.8

[56] References Cited

U.S. PATENT DOCUMENTS 4,486,530 12/1984 David et al. .......................... 435/7
5,298,393 3/1994 Urushizaki et al. .................. 435/7.1

FOREIGN PATENT DOCUMENTS 0245520 6/1987 European Pat. Off. .

OTHER PUBLICATIONS

I. Y. Wang et al., "Multiple Ya Subunits of Glutathione S–Transferase Detected by Monoclonal Antibodies", Articles of Bichemistry and Biophysics, vol. 245, No. 2, Mar. 1986, pp. 543–547.
Shiratori, et al., Cancer Res., 1987, 47(24, Pt. 1), 6806–9, "Immunohistochemical Detection of the Placental Form of Glutathione S-transferase in Dysplastic and Neoplastic Human Uterine Cervix Lesions".

Primary Examiner—Christine M. Nucker
Assistant Examiner—Laurie Scheiner
Attorney, Agent, or Firm—Wenderoth, Lind & Ponack

[57] ABSTRACT

A method of immunologically determining human acid glutathione S-transferase in a human assay sample, which comprises bringing the assay sample into contact with a first antibody bound to an insoluble solid carrier and a labelled second antibody, either the first or second antibody being a polyclonal antibody capable of recognizing human acid glutathione S-transferase or an equivalent fragment of the polyclonal antibody, and the other antibody being a monoclonal antibody capable of specifically recognizing human acid glutathione S-transferase or an equivalent fragment of the monoclonal antibody, a method of diagnosing cancer in a human digestive organ by using the above method, a reagent therefor, a kit therefor and a monoclonal antibody for use therein.

21 Claims, 13 Drawing Sheets

Fig. 3
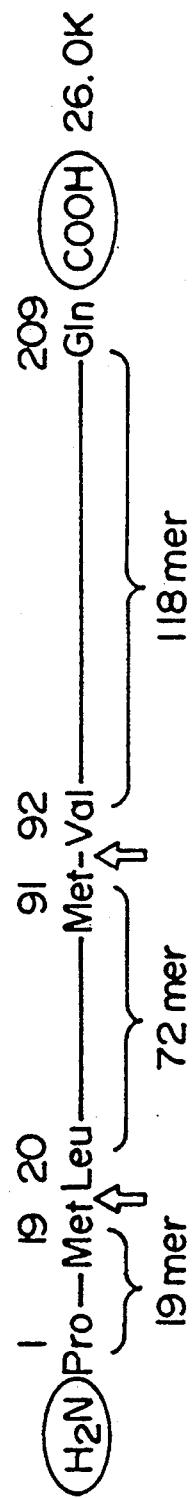
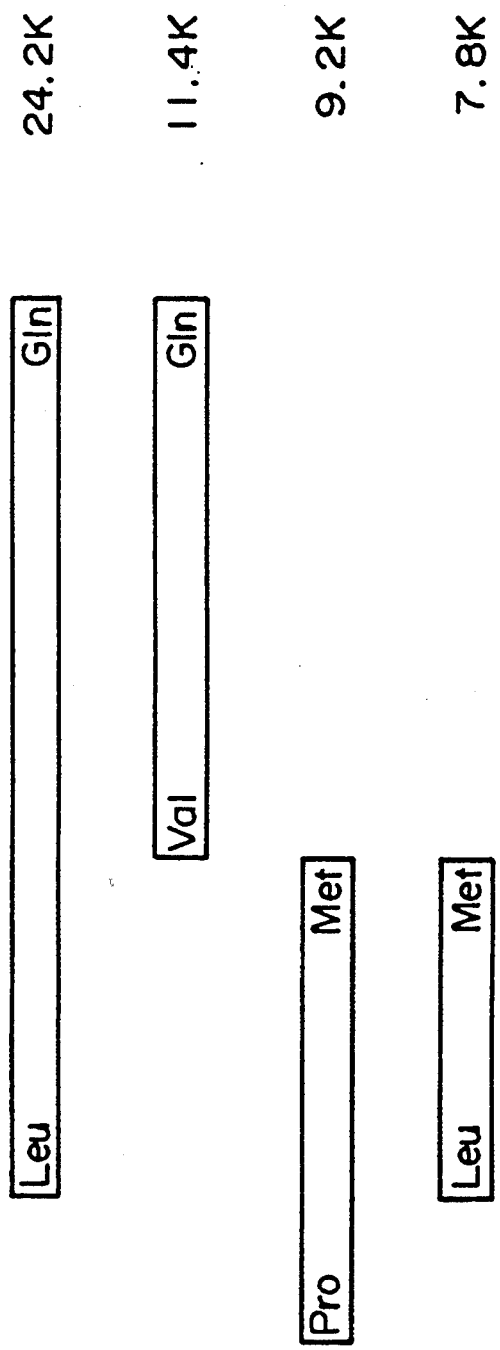

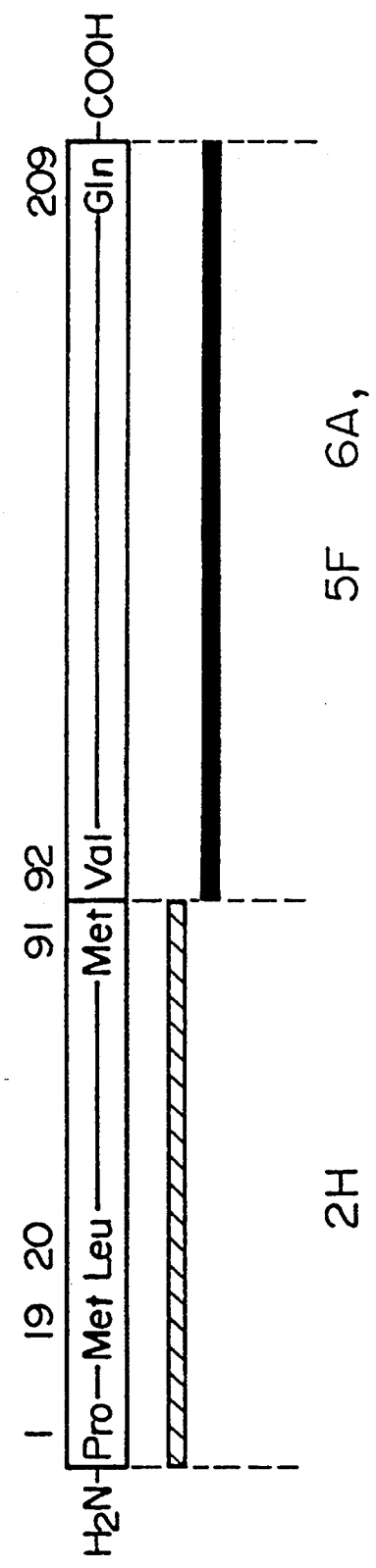

Fig. 5(a)
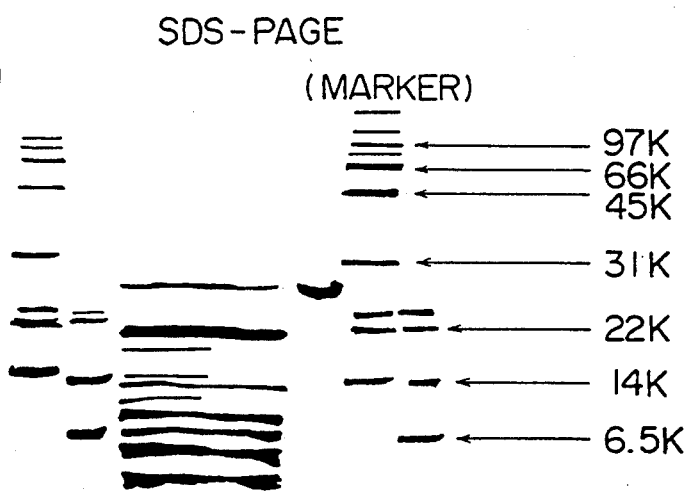
Fig. 5(b) 5μl, 10μl, 20μl, 30μl MATERIAL FIXED TRYPSIN
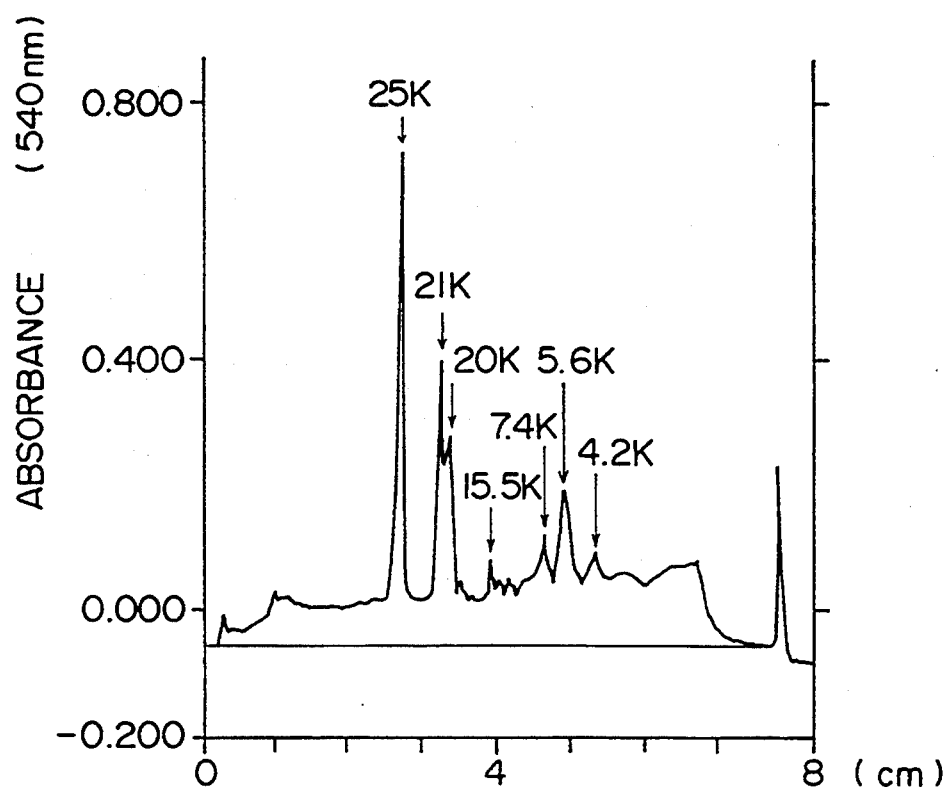

PCA 2H 6A 5F

GST-π MOLECULE OF THE MATERIAL

| 1 | 2 | 3 | 4 | 5 | 6 | 7 | 8 | 9 | 10 |
|---|---|---|---|---|---|---|---|---|----|
| Pro | Pro | Tyr | Thr | Val | Val | Tyr | Phe | Pro | Val |

| 11 | 12 | 13 | 14 | 15 | 16 | 17 | 18 | 19 | 20 |
|----|----|----|----|----|----|----|----|----|----|
| Arg | Gly | Arg | Cys | Ala | Ala | Leu | Arg | Met | Leu |

Fig. 16(a)

```
1                                                      10
(N)-Pro Pro Tyr Thr Val Val Tyr Phe Pro Val Arg Gly Arg Cys
         20
Ala Ala Leu Arg Met Leu Ala Asp Gln Gly Gln Ser Trp Lys
30                               40
Glu Glu Val Val Thr Val Glu Thr Trp Gln Glu Gly Ser Leu Lys
         50
Ala Ser Cys Leu Tyr Gly Gln Leu Pro Lys Phe Gln Asp Gly Asp
60                               70
Leu Thr Leu Tyr Gln Ser Asn Thr Ile Leu Arg His Leu Gly Arg
         80
Thr Leu Gly Leu Tyr Gly Lys Asp Gln Gln Glu Ala Ala Leu Val
90                               100
Asp Met Val Asn Asp Gly Val Glu Asp Leu Arg Cys Lys Thr Ile
```

Fig. 16(b)

```
                                         110
Ser Leu Ile Tyr Thr Asn Tyr Glu Ala Gly Lys Asp Asp Tyr Val
120                                      130
Lys Ala Leu Pro Gly Gln Leu Lys Pro Phe Glu Thr Leu Leu Ser
                                         140
Gln Asn Gln Gly Gly Gly Thr Phe Ile Val Gly Asp Gln Ile Ser
150                                      160
Phe Ala Asp Tyr Asn Leu Leu Asp Leu Leu Ile His Glu Val
                                         170
Leu Ala Pro Gly Cys Leu Asp Ala Phe Pro Leu Leu Ser Ala Tyr
180                                      190
Val Gly Arg Leu Ser Ala Arg Pro Lys Leu Lys Ala Phe Leu Ala
                                         200                        209
Ser Pro Glu Tyr Val Asn Leu Pro Ile Asn Gly Asn Gly Lys Gln-(C)
```

METHOD OF DETERMINING HUMAN ACID GLUTATHIONE S-TRANSFERASE, REAGENT, THEREFOR, KIT THEREFOR, METHOD OF DIAGNOSING CANCER IN DIGESTIVE ORGANS, AND MONOCLONAL ANTIBODY FOR USE THEREIN

This application is a continuation of now abandoned application, Ser. No. 07/731,367, filed Jul. 16, 1991, which is a continuation-in-part of now abandoned application, Ser. No. 07/304,648 filed Feb. 1, 1989.

This invention relates to a method of determining human acid glutathione S-transferase in a human assay sample, a reagent therefor, a kit therefor, a method of diagnosing cancer in digestive organs, and to a monoclonal antibody. Particularly, it relates to a method of determining human acid glutathione S-transferase in an assay sample immunologically using an antibody and thus diagnosing cancer in digestive organs, a reagent therefor, a kit therefor, and a monoclonal antibody for use therein.

Glutathione S-transferase (to be sometimes abbreviated "GST") is known as a detoxifying enzyme which catalyzes conjugation reactions between various substances invading the living body or metabolites in the body and reduced glutathione. Many of these substances and metabolites react with proteins or nucleic acids in the body to become a cause of various lesions, for example carcinogenesis. The reactivity of these substances is neutralized by conjugation with glutathione, and they are converted into more water-soluble products which are metabolized, for example, in the liver and finally excreted out of the body.

GST occurs widely in many biological species including mammals, particularly in abundance in the cytoplasm of liver, and in varying amounts in the spleen, kidneys, lungs, brain, skeletal muscle, testicles and small intestines. Special molecular species have been isolated from the placenta or red blood cells. Generally, GST is composed of many enzymes and has species specificity and specificity for organs or tissues.

In humans, two types, i.e. basic GST and acid GST, are known [J. Biol. Chem., 259, 12444 (1984)]. Human basic GST has an isoelectric point. (pI) of 7 to 9, and is composed of two subunits both having a molecular weight of about 23,000. Five molecular species, α, β, γδ, ε, are known to exist in human basic GST. These molecular species exist in the liver and also in the kidneys, testicles, small intestines, brain and lungs of normal healthy adults.

Human acid GST has an isoelectric point (pI) of 4 to 5 and is composed of two subunits both having a molecular weight of about 22,000. A species π of human acid GST is known to exist in placenta, and its species ρ is known to exist in the red blood cells. It hardly exists in the liver of normal healthy adults.

It was reported recently in the following literature that GST which cannot be detected in normal cells exist in considerably large amounts in cancer cells of organs of a certain kind.

(i) D. J. Meyer, D. Peale, K. H. Tan, B. Coles and B. Ketherer examined glutathione S-transferases in primary rat hepatoma, and reported the isolation of a form with glutathione peroxidase activity [FEBS Lett., 184; 139-143 (1985)].

(ii) H. Sherman, J. A. Campbell, S. A. Timuss, M. C. Ker and R. E. Kirsch reported glutathione S transferase in heptecellular carcinoma [Hepatology 3,170-176 (1983)].

(iii) C. D. Dillio, E. D. Boccio, A. Aceto and G. Feririci reported the alteration of glutathione transferase isoenzyme concentrations in human renal carcinoma [Carcinogenesis 8,861-864 (1987)].

(iv) T. Kano, M. Sakai and M. Muramatsu reported the presence of glutathione S-transferase in human colon cancer cells [Cancer Res., 47, 5626-5630 (1987)].

(v) C. Kodate, A. Fukushi, T. Narita and H. Kudo reported the presence of glutathione S-transferase in human stomach cancer cells [Gann., 77, 226-229].

(vi) Bohn reported the presence of glutathione S-transferase in biliary tract cancer cells [Oncodevelop. Biol. Med., 2, 141-153 (1981)].

These publications state that glutathione S-transferase is not present, or can hardly be detected, in the cells of digestive organs such as liver, colon, stomach and biliary tract, but is present in detectable amounts in cancer cells of these organs. These publications merely determined the presence of glutathione S-transferase by assaying cancer cells or the culture supernatant of cancer cells.

On the other hand, a method was proposed by which two sorts of anti-human acid GST monoclonal antibodies are used to determine acid GST in a human assay sample, particularly a human serum sample (see the specification of WO 87/03377). This method utilizes the inherent specificities of the monoclonal antibodies, or their reactivity with only a specific epitope of a specific antigen. It is difficult however to find out a combination of two sorts of monoclonal antibodies which have high affinity and can actually be used in determining tiny amounts of human acid GST.

The present inventors attempted to use a well-practiced immunological method involving the use of a polyclonal antibody for the determination of human acid GST. By this method, however, it is difficult to determine minute amounts of human acid GST in a human assay sample stably with specificity and a certain level because human acid GST is an enzyme including many kinds of isozymes and the quality of the polyclonal antibody itself varies depending upon its source of procurement.

Investigations of the present inventors showed that the method of determining human acid GST by using a combination of two kinds of monoclonal antibodies and the method of determining human acid GST using a polyclonal antibody discussed above require further improvement in order to use them for the stable determination of minute amounts of human acid GST in a human assay sample, particularly a human serum or plasma sample, and particularly for the practical utilization of a result of the measurement in diagnosing a certain lesion.

The present inventors found that usually, human acid GST is not present, or present only in a tiny amount in a body fluid, particularly plasma, of a normal subject, but when a digestive organ is attacked by cancer, glutathione S-transferase comes into being in the body fluid and becomes detectable, or its amount in the body fluid increases.

This fact suggests the possible utilization of the amount of human acid GST in a human body fluid, particularly blood, as a tumor marker having specificity for digestive organ cancers such as liver cancer, stomach cancer, colon cancer, and esophagus cancer.

The present inventors also found that acid GST is present in the body fluids of patients with digestive organ cancer in detectable amounts or in larger amounts than acid GST in normal subjects.

Accordingly, if an immunological assay system can be provided .which can recognize acid GST produced by commonly proliferating cells of digestive organs in liver cancer cells, stomach cancer cells, esophagus cancer cells, etc. irrespective of the type of the cancer cells, it would of course be able to be utilized for determining human acid GST in a human assay sample such as a human serum or plasma sample, and permit simple diagnosis of cancer of digestive organs.

Although the amount of acid GST in a body fluid of a patient with digestive organ cancer is larger than that in a body fluid of a normal subject, its absolute amount is very minute (for example, several ng/ml to several hundred ng/ml). It is essential therefore to the above diagnosis of cancer to develop a method of determining a minute amount of acid GST with simplicity and high sensitivity.

It is an object of this invention therefore to provide a method of determining human acid GST in a human assay sample by immunological means with stability and high sensitivity.

Another object of this invention is to provide a simple method of determining human acid GST in a human assay sample commonly with high sensitivity independently of the type of proliferating cells of digestive organs which produce acid GST.

Still another object of this invention is to provide a method of diagnosing cancer in a human digestive organ which comprises determining the amount of human GST in a human assay sample, particularly human serum sample, and diagnosing the onset of cancer in a human digestive organ, the state of its progress or its cure on the basis of the measured amount of human GST.

Yet another object of this invention is to provide an assay reagent and its kit for determining human acid GST stably with high sensitivity which can be used in the above determination method and the diagnosing method.

A further object of this invention is to provide a method which comprises taking out a tissue from a human digestive organ, determining the amount of human acid GST in the tissue, and diagnosing cancer in the digestive organ.

A still further object of this invention is to provide a practical and simple immunological method of determining human acid GST and a reagent and a kit therefor which help to discover the onset of cancer in a human digestive organ or cancer in the organ in the early stage.

Other objects of the invention will become apparent from the following description.

The foregoing objects of the invention along with its advantages are basically achieved by 1. a method of immunologically determining human acid glutathione S-transferase in a human assay sample, which comprises bringing the assay sample into contact with a first antibody bound to an insoluble solid carrier and a labelled second antibody, either the first or second antibody being a polyclonal antibody capable of recognizing human acid glutathione S-transferase or an equivalent fragment of the polyclonal antibody, and the other antibody being a monoclonal antibody capable of specifically recognizing human acid glutathione S-transferase or an equivalent fragment of the monoclonal antibody; and 2. a method of diagnosing cancer in a human digestive organ, which comprises
(i) using a first antibody bound to an insoluble solid carrier and a labelled second antibody, either the first or second antibody being a polyclonal antibody capable of recognizing human acid glutathione S-transferase or an equivalent fragment of the polyclonal antibody, and the other antibody being a monoclonal antibody capable of specifically recognizing human acid glutathione S-transferase or an equivalent fragment of the monoclonal antibody,
(ii) bringing a human assay sample into contact with the first and second antibodies,
(iii) determining the amount of human acid glutathione S-transferase contained in the sample, and
(iv) diagnosing the onset of cancer in a human digestive organ, the state of its progress or its cure on the basis of the determined amount of human acid glutathione S-transferase.

According to this invention, human acid GST present in very small amounts in a human assay sample can be determined stably with high sensitivity, and the method and the kit used for it are simple. As stated above, the amount of human acid GST in an assay sample taken from a patient with cancer in digestive organs is minute but larger than that of a sample taken from a normal subject. The method of this invention can determine this minute amount of human acid GST accurately with high sensitivity and can help to diagnose cancer in digestive organs, particularly the discovery of cancer.

In Example 6 given hereinbelow, the amount of human acid GST in serum samples of normal subjects and patients with various digestive organ cancers was determined by the method of this invention. The result shows that it is about 11.2 ng/ml on an average for the normal subjects, whereas it is about 27.5 ng/ml for the patient with esophagus cancer, about 34.7 ng/ml for the patient with stomach cancer, about 29.5 ng/ml for the patient with colon cancer, and about 26.9 ng/ml for the patient with liver cancer. Thus, significant differences were clearly seen in the amount of human acid GST between the normal subjects and the cancer patients. This shows a clear correlation between the amount of human acid GST and cancer in digestive organs.

Another interesting fact is that sera of patients with gastrointestinal diseases which are not cancer, such as gastric ulcer, colitis, cholelithiasis, hepatitis and liver cirrhosis only contained human acid GST in amounts which statistically do not differ significantly from the amount of human acid GST in a normal subject. These facts have led us to believe that the determination of human acid GST in a human assay sample is very useful for the diagnosis of cancer in digestive organs.

One important feature of the assay system in accordance with this invention is that a tiny amount of human acid GST ascribed mainly to cancer in various digestive organs can be commonly measured accurately.

Heretofore, there has been no method nor reagent system or kit by which the tiny amounts of human acid GST in assay samples taken from normal subjects and patients with digestive organ cancer can be accurately measured and differentiated.

The term "digestive organs" used in the present specification and the appended claims denotes organs relating to the digestive system, and more specifically stomach, esophagus, colon, liver and cholecyst. The determination of human acid GST in accordance with this invention is effective for the diagnosis of cancer in these organs, specifically checking for carcinogenesis, monitoring of the progress of cancer, and determination of the cure of cancer as a result of treatment.

Diagnosis of cancers by the determination of human acid GST in accordance with this invention applies not only to cancers in the above digestive organs, but also to other diseases, particularly other cancers, which show an increased level of acid GST over normal subjects.

The human assay sample used in the determination of human acid GST may be various human tissues or body fluids, and they include, for example, serum, plasma, ascites, tissue cells of the digestive organs, and culture supernatants of these cells. A human serum or plasma sample is most preferred.

It is known that human acid GST is composed of two subunits having a molecular weight of about 22,000.

In human acid GST-producing cells or culture supernatants thereof, human acid GST is believed to be composed of two subunits. Many experiments, however, show that in a fraction of blood obtained by ordinary centrifugation or the like, for example serum or plasma, human acid GST, in many cases, exists as a single subunit, although no clear cause of this has been known. Accordingly, the present inventors presume from the results of many experiments that human acid GST in the fractionated serum or plasma exits as a single subunit.

The assay system of this invention permits determination of human acid GST whether it is composed of two subunits or only a single subunit. However, the human assay sample to be determined actually is, in many cases, human serum or plasma, and human acid GST in such a sample exists mostly as a single subunit. Accordingly, the amount of human acid GST in the assay sample can be calculated on the basis of a calibration curve prepared under the assumption that human acid GST is composed of a single subunit.

On the other hand, when it is desired to determine the amount of human acid GST in human acid GST-producing cells, it is reasonable to prepare a separate calibration curve and calculate the amount of human acid GST on the basis of the calibration curve since human acid GST in these cells are believed to be composed of two subunits.

In any case, when the amount of human acid GST in a normal subject is compared with that in a patient with cancer in a digestive organ using the same kind of assay samples (for example, serum or plasma), a marked difference in the amount of human acid GST is observed so long as the same calibration curve is used.

The present invention will be described below in more detail.

Characteristics and Preparation of the Polyclonal Antibodies Used in the Invention The polyclonal antibody used in this invention is obtained as an antibody component of anti-human acid GST anti-serum which is obtained by immunizing an animal with human acid GST-$\pi$ as an antigen by a known method. Goat anti-human acid GST-polyclonal antibody and rabbit anti-human acid GST-polyclonal antibody are preferably used in this invention. Polyclonal antibodies purified by affinity chromatography of the antigen are more preferred.

Among these polyclonal antibodies, those which react with a region of the amino acid sequence of human placenta-derived GST ("GST-$\pi$" hereinafter) molecules ranging from an amino acid residue (Val), 92nd from the N-terminus, to an amino acid residue (Gln), 209th (C-terminus), are used advantageously.

The equivalent fragment of the polyclonal antibody as used in this invention means a fragment of the above polyclonal antibody which reacts with human acid GST in substantially the same way as in the reaction of the polyclonal antibody with human acid GST (antigen). Specifically, Fab, Fab' and F(ab')$_2$, above all Fab' or F(ab')$_2$, are preferred.

Characteristics and Preparation of the Monoclonal Antibodies Used in the Invention The monoclonal antibody to human placenta-derived acid GST (GST-$\pi$) used in this invention is a monoclonal antibody which specifically recognizes human placenta-derived human acid GST (GST-$\pi$) produced by proliferating cells of cancer cells of digestive organs such as human liver, stomach and esophagus, and preferably has a common epitope in human acid GST produced by these cancer cells.

Preferably, the monoclonal antibodies used in this invention are of the IgG class, and are advantageously mouse antibodies. The monoclonal antibodies used in this invention specifically recognize human acid GST, but do not at all recognize, and therefore do not cross-react with, human basic GST.

Most preferably, the present invention provides the following three monoclonal antibodies.

(a) A monoclonal antibody to human placenta-derived glutathione S-transferase, which can specifically recognize a region of the amino acid sequence of human placenta-derived glutathione S-transferase ranging from amino acid residue Pro at the N-terminus to the 44th amino acid residue Lys (this monoclonal antibody may sometimes be abbreviated "monoclonal antibody 2H").

(b) A monoclonal antibody to human placenta-derived glutathione S-transferase, which can specifically recognize a region of the amino acid sequence of human placenta-derived glutathione S-transferase ranging from the 176th amino acid residue Leu from the N-terminus to the 209th amino acid residue Gln (this monoclonal antibody may sometimes be abbreviated "monoclonal antibody 6A").

(c) A monoclonal antibody to human placenta-derived glutathione S-transferase, which can specifically recognize a region of the amino acid sequence of human placenta-derived glutathione S-transferase ranging from the 141st amino acid residue Thr from the N-terminus to the 175th amino acid residue Leu (this monoclonal antibody may sometimes be abbreviated "monoclonal antibody 5F").

The three monoclonal antibodies (a), (b) and (c) have different epitopes in GST-$\pi$ and excellent affinity for the objects of this invention.

These monoclonal antibodies specifically recognize different epitopes of GST-$\pi$, and have inherent characteristic reactivities depending upon the state in which GST-$\pi$ exists, namely depending upon whether it is afloat in a liquid phase or it is fixed to the surface of a solid carrier.

Specifically, the monoclonal antibodies (a) and (b) (monoclonal antibodies 2H and 6A) exhibit reactivity with GST-$\pi$ directly fixed to the surface of a solid carrier and GST-$\pi$ floating in a liquid phase. On the other hand, the monoclonal antibody (c) (monoclonal antibody 5F) shows reactivity with GST-$\pi$ fixed directly on the surface of a solid carrier, but does not show substantial reactivity with GST floating in a liquid phase.

Direct fixation of GST-$\pi$ to the surface of a solid carrier is effected by the following procedure. GST-$\pi$ prepared in a concentration of 1 microgram/ml is added in an amount of 100 microliters to each well of a polystyrene plate (made by Sumitomo Bakelite Company), and left to stand overnight at 4° C. The plate is then washed three times with phosphate buffer (PBS) and after-coated with 1% BSA-PBS to prepare a sample in which GST-$\pi$ is fixed. The reactivities of the monoclonal antibodies are examined by using this sample.

The monoclonal antibodies to human acid GST used in this invention may be obtained by methods described below.

Preferably, antibody-producing cells of an animal immunized with human placenta-derived GST (GST-$\pi$) are fused with myeloma cells to give a hybridoma capable of producing a monoclonal antibody to GST-$\pi$. Then, the hybridoma and/or a cell line derived from it is cultured, and the resulting monoclonal antibody to GST-$\pi$ is recovered from the culture.

Human GST-$\pi$ used for immunization is composed of two subunits both having a molecular weight of about 22,000, shows a single band in sodium dodecyl sulfate polyacrylamide gel electrophoresis (SDS-PAGE) and has an isoelectric point (pI) of 4 to 5.

The hybridoma capable of producing a monoclonal antibody which recognizes human GST-$\pi$ can be produced by a cell fusion technique known per se. An animal such as monkey, horse, bovine, goat, sheep, rabbit, rat and mouse is immunized with human GST-$\pi$, and antibody-producing cells (lymphocytes) are taken from the spleen, lymph nodes, etc. of the immunized animal. The antibody-producing cells are then fused with myeloma cells of man or another animal. It is convenient to use mouse myeloma cells such as P3-X63-Ag8, P3X63-Ag8-U1, P3-NS1/1-Ag4-1, P3-X63-AgS-6.5.3, SP2/0-Ag14, Fo and MPC11-45.6TG1.7 of BALB/C mice.

The cell fusion conditions are, for example, as follows: The antibody-producing cells and the myeloma cells are mixed in a mixing ratio of from 10:1 to 1:10, preferably from 1:1 to 1:3, and a suitable cell fusion solution such as RPMI 1640 containing about 35% of polyethylene glycol having a molecular weight of about 1,000 to 6,000 and 7.5% of dimethyl sulfoxide is added. The mixture is stirred at room temperature to 37° C. for 1 to several minutes. The mixture is then gradually diluted with RPMI 1640 containing 10% of bovine fetal serum. After washing, the diluted mixture is adjusted to a cell density of 1 to $5 \times 10^5$/ml with a HAT (hypoxanthine-aminopterine-thymidine) selective medium. The resulting medium was added to a 96-well plate at a rate of 0.2 ml per well, and incubated at 35° to 38° C. for 2 to 3 weeks in air containing 5% $CO_2$. In the HAT medium, only the hybridoma survived, and 8-azaguanine-resistant myeloma cells and myeloma/myeloma fused cells cannot survive (the unfused antibody-producing cells die in several days). Then from the hybridoma colonies, only those colonies which secrete a monoclonal antibody specific for human GST-$\pi$ are selected. This screening step can be carried out by examining the hybridoma colonies in accordance with an enzyme-linked immunosorbent assay (ELISA) to determine whether the monoclonal antibodies produced by the hybridoma react with human GST-$\pi$. The hybridoma colonies which secrete the desired monoclonal antibody are then cloned. This step can be carried out by using a limiting dilution method. About 2 to 3 weeks later, the colonies grown in the 96-well plate are picked up and again examined for antibody activity on human GST-$\pi$ by ELISA. The elected hybridoma colonies are cultured to produce a monoclonal antibody specific for human GST-$\pi$.

Another method of obtaining the monoclonal antibody comprises transfecting the antibody-producing cells with Epstein-Barr virus (E-B virus for short) to prepare transformed cells, culturing the transformed cells and/or a cell line derived therefrom, and recovering a monoclonal antibody having the property of binding to human GST-$\pi$ from the culture.

E-B virus belongs to a virus of a group of herpes viruses, which is considered to be the cause of Burkitt's lymphoma and rhinal and throat cancer. The antibody-producing cells are infected with E-B virus, and about 2 to 3 weeks later, incubated in a 5% $CO_2$ incubator to form many heterogeneous colonies of transformed cells. From these colonies, only those colonies which secrete a monoclonal antibody specific for human GST-$\pi$ are selected by the same method as described above. The selected colonies are cloned to form the desired transformed cells.

Then, the selected hybridoma or transformed cells are cultured to produce the desired specific monoclonal antibody. The hybridoma or transformed cells which produce an antibody recognizing human GST-$\pi$ and are selected by cloning may be frozen and stored, or may be cultured in quantities by a suitable method. From the culture supernatant, the monoclonal antibody specifically binding to human GST-$\pi$ can be obtained. It is also possible to transplant the cells into an animal to form a tumor, and obtain the desired antibody from the ascites or serum of the animal. The monoclonal antibody may be purified by, for example, affinity chromatography using protein A.

Specific examples of the hybridomas produced include hybridomas 6A and 2H, which secret the monoclonal antibodies 6A and 2H of the present invention, respectively, and which have been deposited with the Fermentation Research Institute (FRI), 1-3, Higashi 1-chome, Tsukuba-shi, Ibaraki-ken 305 Japan, on July 18, 1990 under deposit nos. FERM-3023 and FERM-3024, respectively, under the Budapest Treaty.

The monoclonal antibodies used in this invention are prepared and purified by the above methods, and are useful for assaying human acid GST or diagnosing cancer of digestive organs. Equivalent fragments of these monoclonal antibodies may also be used in the above assay and diagnosis. The "equivalent fragments" mean fragments which show reactivity with human acid GST in substantially the same way as the corresponding monoclonal antibodies. Specifically, they are Fab, Fab' and F(ab')$_2$, especially preferably Fab' and F(ab')$_2$.

In the present invention, a monoclonal antibody which corresponds to the monoclonal antibody produced by FERM BP-3023 is defined as one which specifically recognizes a region of the amino acid sequence of human placenta-derived glutathione S-transferase which ranges from the 176th amino acid residue Leu to the 209th amino acid residue Gln from the N-terminus.

The immunological method of determining human acid GST in a human assay sample, and the assay reagent and the kit used in it in accordance with this invention will be described specifically.

Method of immunologically determining human acid GST

A first antibody to human acid GST is fixed to a suitable insoluble solid carrier such as a plastic receptacle (the antibody will be referred to as the "fixed antibody"). Then, the surface of the insoluble solid carrier is coated with a suitable substance (such as bovine serum albumin) to void a non-specific combination of the insoluble solid carrier with the reagent or the assay sample.

The insoluble solid carrier to which the first antibody is fixed is then contacted with the human assay sample at a fixed temperature for a fixed period of time to perform reaction. During this time, human acid GST in the assay sample binds to the fixed antibody (first antibody). After washing with a suitable washing solution, a solution (such as an aqueous solution) of a second antibody to human acid GST, which is labelled with a suitable labelling substance (such as an enzyme) is contacted and reacted with human acid GST (antigen) bound to the fixed antibody in the insoluble solid carrier at a fixed temperature for a fixed period of time. The insoluble solid carrier is washed with a suitable washing solution, and the amount of the labelling substance labelled on the second antibody on the insoluble solid carrier is measured.

Either one of the first and second antibodies is a polyclonal antibody, and the other, a monoclonal antibody.

The above reaction may also be carried out by mixing the fixed antibody (first antibody), the labelled antibody (second antibody) and the assay sample containing human acid GST simultaneously and contacting the three simultaneously at a fixed temperature for a fixed period of time.

Thus, the amount of human acid GST in the human assay sample can be calculated from the amount of the labelling substance on the second antibody.

Assay Reagent and Kit

The assay reagent for immunological determination of human acid GST is composed of the antibody bound to the insoluble solid carrier and the labelled antibody.

The kit for immunological determination of human acid GST comprises the assay reagent and as adjuvants for utilizing the assay reagent efficiently and conveniently, a dissolving agent for dissolving a solid reagent or a liquid assay sample, for example, a washing agent for washing away the antigen and antibody nonspecifically bound to the insoluble solid carrier, and when an antibody labelled with an enzyme is used, a substrate for measuring enzyme activity and a reaction stopper therefor, and other adjuvants usually employed in other immunological assay kits.

Examples of the insoluble solid carrier used in the method of immunologically determining human acid GST and the kit include polymers such as polystyrene, polyethylene, polypropylene, polyesters, polyacrylonitrile, fluorine-containing resins, crosslinked dextran and polysaccharides, paper, glass, metals, agarose, and combinations of these.

The insoluble solid carrier may be in various shapes, such as a tray, a sphere, a fiber, a rod, a disc, a receptacle, a cell and a test tube.

Advantageously, the labelling substance in the labelled antibody may be, for example, an enzyme such as peroxidase, alkaline phosphatase or beta-D-galactosidase; a fluorescent substance such as fluorescent isothiocyanate and phycobiliprotein, a luminescent substance such as isolucinol, lucigenin, or a radioactive substance such as $^{125}I$, $^{131}I$, $^{14}C$ and $^{3}H$. Other labelling substances which are generally used in immunological assay may also be used in this invention.

When the labelling agent is an enzyme, a substrate for measuring its activity and as required, a coloring agent may be used.

When peroxidase is used as the enzyme, $H_2O_2$ is used as the substrate and ammonium 2,2'-azinodi-(3-ethyl-benzothiazolinesulfonate) (ABTS), 5-aminosalicyclic acid, o-phenylenediamine, 4-aminoantipyrine and 3,3',5,5'-tetramethylbenzidine may be used as the coloring agent. When alkaline phosphatase is used as the enzyme, o-nitrophenyl phosphate is used as the substrate. When beta-D-galactosidase is used as the enzyme, fluorescein-di-(beta-D-galactopyranoside) and 4-methylumbelliferyl-beta-D-galactopyranoside may be used as the substrate.

Preferably, in the determination of human acid GST in accordance with this invention, one of the first antibody and the labelled second antibody is the above polyclonal antibody and the other is the monoclonal antibody 2H or monoclonal antibody 6A because this combination gives higher sensitivity.

An especially preferred combination is a combination of the polyclonal antibody as the first antibody and the monoclonal antibody 2H or monoclonal antibody 6A as the labelled second antibody.

These combinations in which the polyclonal antibody and/or the monoclonal antibody are fragments equivalent therefore are also preferred.

Use of an Antigen-Antibody Reaction Regulating Agent in Immunological Assay

In order to inhibit a non-specific reaction without substantially reducing the specific reaction in the assay of human acid GST in the human assay sample in accordance with this invention, an antigen-antibody reaction adjusting agent to be described below may be used under the following conditions. This permits immunological determination of human acid GST with higher sensitivity, and is preferred for the objects of this invention.

In this method, a protein having an average molecular weight of 16,000 to 50,000 and an isoelectric point of 1.0 to 5.0 or a mixture containing it is added to the immunological reaction solution as an antigen-antibody reaction regulating agent, and the final concentration of the antigen-antibody reaction regulating agent in the immunological reaction solution is adjusted to 0.02 to 0.9% by weight.

The "average molecular weight" of the protein used in this invention is measured by an osmotic pressure method by which the average molecular weight of the protein is measured by utilizing the fact that when a solution of a polymer and a solvent are contacted with each other via a semipermeable membrane which is permeable to the polymer solution and the solvent but impermeable to the dissolved polymer, the difference in osmotic pressure between the two liquids becomes a parameter of the molecular weight of the polymer. It is measured at 4° C. by using a 6.66M urea solution as the solvent.

The "isoelectric point" of the protein denotes a value measured by a chromatofocusing method which separates a protein according to its isoelectric point. Specifically, it is measured by using a column (0.5 cm in diameter and 45 cm in length) filled with a gel of PBE 94 (produced by Pharmacia Co.) and 0.025M imidazole HCl (pH 7.4) as an eluent.

Examples of the protein used as the antigen-antibody reaction regulating agent include casein, pepsin, oveglycoprotein and orosomucoid. When a protein having a molecular weight of less than 16,000 is used, non-specific adsorption tends to increase. On the other hand, if the molecular weight of the protein exceeds 50,000, the decrease of the immunologically non-specific reaction tends to be insufficient, and the specific immunological reaction tends to decrease. Accordingly, the molecular weight of the protein used is 16,000 to 50,000, preferably 20,000 to 46,000.

If the protein added has an isoelectric point of more than 5.0, the non-specific adsorption increases, and if it has an isoelectric point of less than 1.0, the specific reaction is inhibited. Accordingly, the protein used as the antigen-antibody reaction regulating agent has an isoelectric point of 1.0 to 5.0, preferably 1.2 to 4.8.

A mixture containing the above protein may be used as the antigen-antibody reaction regulating agent. Such a mixture may comprise 10 to 60% by weight, preferably 20 to 50% by weight, of the protein and 30 to 80% by weight, preferably 40 to 60% by weight, of a sugar (such as lactose) as main components, and fats (e.g., 0.5 to 2% by weight), ashes (e.g., 5 to 12% by weight) and water (e.g., 2 to 8% by weight). A typical example of such a mixture is skimmed milk. Skimmed milk contains casein as the protein, but is characterized by having better dispersibility in the immunological reaction solution, a higher non-specific binding effect per unit weight of the protein, and better preservability (less prone to form a precipitate) at 4° C. than casein used singly. The skimmed milk may be defatted milk of any type and origin. Most typically, it is commercial skimmed milk produced by Difco Co.

The protein solution (such as a skimmed milk solution) is prepared by the following procedure. A protein or its mixture (e.g., skimmed milk) in a suitable concentration is added to phosphate-buffered physiological saline, and the mixture is stirred for about 1 hour. The mixture is then ultrasonicated to give a solution which, for example, passes through a 0.45 micron millipore membrane.

Immunelogical assay was carried out using protein solutions (or skimmed milk solutions) of various concentrations. When a protein solution (or a skimmed milk solution) having a concentration of less than 0.02% by weight was used, a non-specific reaction markedly increased in spite of the absence of an antigen. Accordingly, the lower limit to the concentration of the protein should be 0.02% by weight. If the concentration exceeds 0.9% by weight, the specific immunelogical reaction decreases and the storage stability of the protein solution in a refrigerator tends to be reduced. Accordingly, the upper limit of the concentration of the protein should be 0.9% by weight. In view of the above two facts, the concentration of the protein which ensures the stability of the reagent and effectively reduces the non-specific reaction is suitably within the range of 0.02 to 0.9% by weight, preferably 0.05 to 0.7% by weight.

Determination of Human Acid GST by Tissue Staining and Diagnosis of Cancer.

The present invention not only provides an immunelogical assay method in accordance with the so-called sandwich method and a kit therefor but also a method of determining human acid GST by tissue staining and a monoclonal antibody used therefor.

In this embodiment, a tumor tissue sample is taken from a digestive organ or other organ, and stained by a known method using the monoclonal antibody in accordance with this invention to determine the amount of human acid GST in the tissue cells. The result of this determination permit diagnosis of cancer.

According to one embodiment of determination of human acid GST by tissue staining, there is provided a method of diagnosing cancer on a human digestive organ, which comprises (i) extracting a tissue sample from a human digestive organ, (ii) fixing the tissue in paraffin and preparing a thin slice of the fixed tissue, (iii) bringing the thin slice into contact with a monoclonal antibody capable of specifically recognizing human acid glutathione S-transferase, or a fragment equivalent thereto, (iv) bringing the monoclonal antibody or its equivalent fragment into contact with a dye capable of staining it, (v) washing and removing the unreacted monoclonal antibody or its equivalent fragment and the dye, (vi) observing the stained state of the tissue, and (vii) thereby diagnosing the onset of cancer in the organ from which the tissue is taken, the state of its progress or its cure.

A monoclonal antibody to human placenta-derived glutathione S-transferase, which can specifically recognize a region of the amino acid sequence of human placenta-derived glutathione S-transferase ranging from the 141st amino acid residue Thr from the N-terminus to the 175th amino acid residue Leu (monoclonal antibody 5F) is most suitable as the monoclonal antibody used in the above tissue staining.

Lane 1: polyclonal antibody (PCA)
Lane 2: monoclonal antibody 2H
Lane 3: monoclonal antibody 6A
Lane 4: monoclonal antibody 5F.

FIG. 3 shows a schematic view of a CNBr-cleaved fragment of GST-$\pi$. Appearance of four fragments is anticipated.

FIG. 4 shows reaction sites of the monoclonal antibodies on the GST-$\pi$ molecule.

FIG. 5, (a) shows an SDS-PAGE pattern of a trypsin-cleaved fragment of a GST-$\pi$ molecule, and FIG. 5, (b) shows scanning of the above SDS-PAGE pattern by a densitometer.

Figure 6:
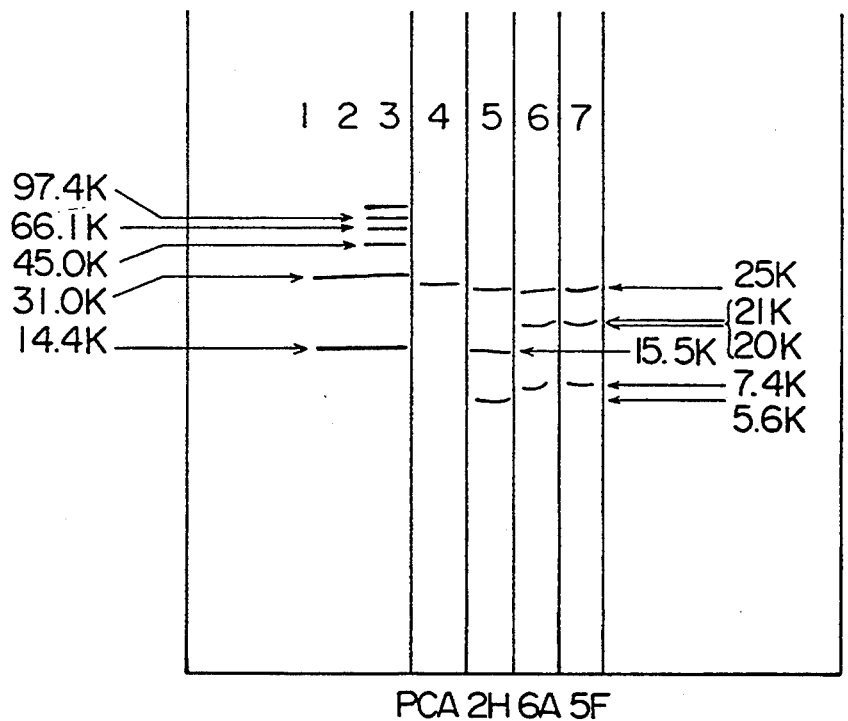

FIG. 6 is a western blotting diagram showing the reactions of various antibody with a trypsin-cleaved fragment of GST-$\pi$.

The following antibodies were reacted in the individual lanes.

Lane 1: polyclonal antibody (PCA)
Lane 2: monoclonal antibody 2H
Lane 3: monoclonal antibody 6A
Lane 4: monoclonal antibody 5F.

Figure 7:
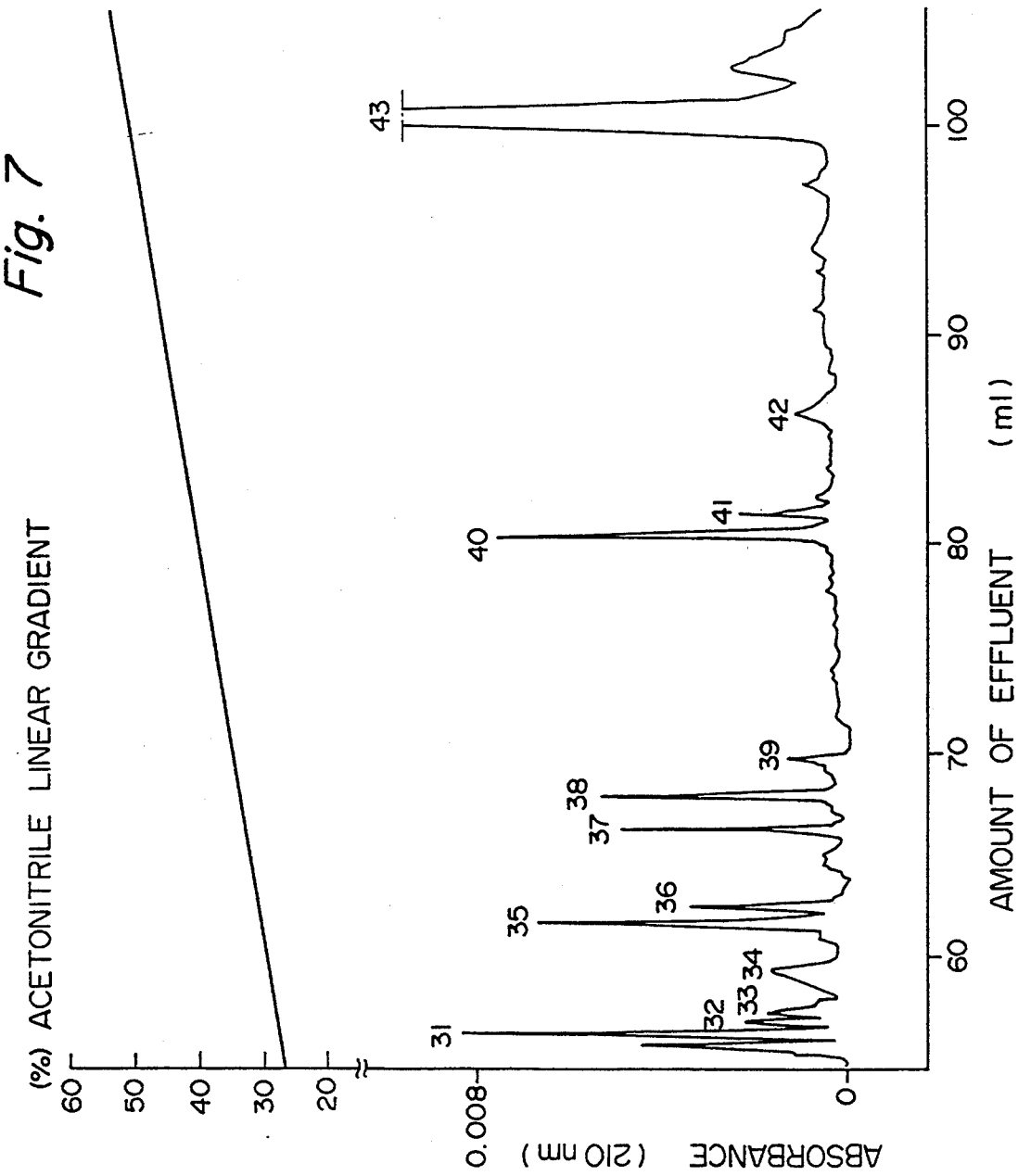

FIG. 7 shows an elution pattern of a trypsin-cleaved fragment of GST-$\pi$ by reverse-phase high-performance liquid chromatography (HPLC) (elution was monitored at 210 nm). Using a TSK gel ODS-ROT column, the fragment was eluted with 0.1% TFA (trifluoroacetic acid) using a linear acetonitrile concentration gradient of 0 to 80% (160 minutes).

Figure 8:
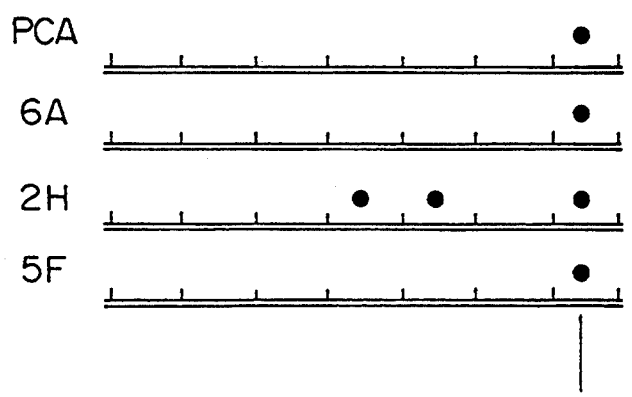

FIG. 8 is a dot blot showing the reactivities Of various antibodies with elution peaks of a trypsin-cleaved fragment, of GST-π. Seven peaks (Nos. 37 to 43) were dot-spotted on a nitrocellulose membrane and the following antibodies were reacted in the individual lanes.
Lane 1: PCA
Lane 2: monoclonal antibody 2H
Lane 3: monoclonal antibody 6A
Lane 4: monoclonal antibody 5F.

Figures 9, 10:
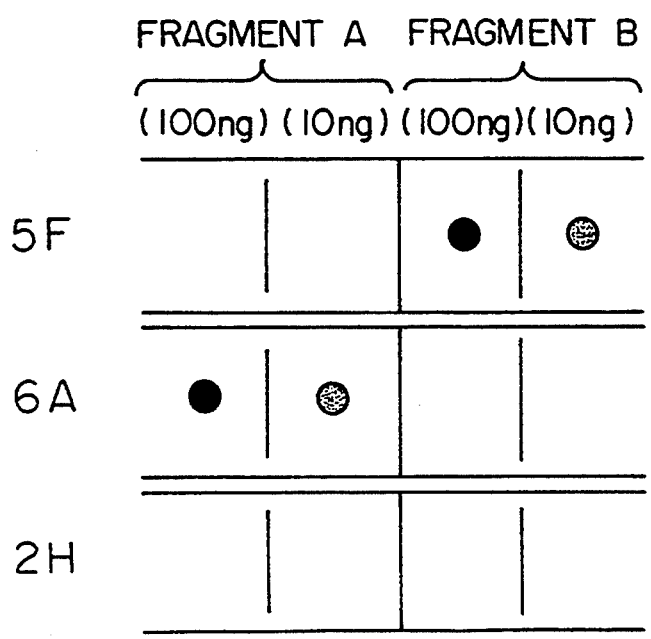

FIG. 9 shows the N-terminus amino acid sequence of peak No. 40 reacted with monoclonal antibody FIG. 10 is a dot blot which shows the reactivities of monoclonal antibodies with GST-π molecule synthetic peptide [$^{176}$Leu-$^{209}$Gln]=fragment A and [$^{141}$Thr-$^{175}$Leu]=fragment B. The following antibodies were reacted in lanes.
Lane 1: monoclonal antibody 5F
Lane 2: monoclonal antibody 6A
Lane 3: monoclonal antibody 2H.

Figure 11A:
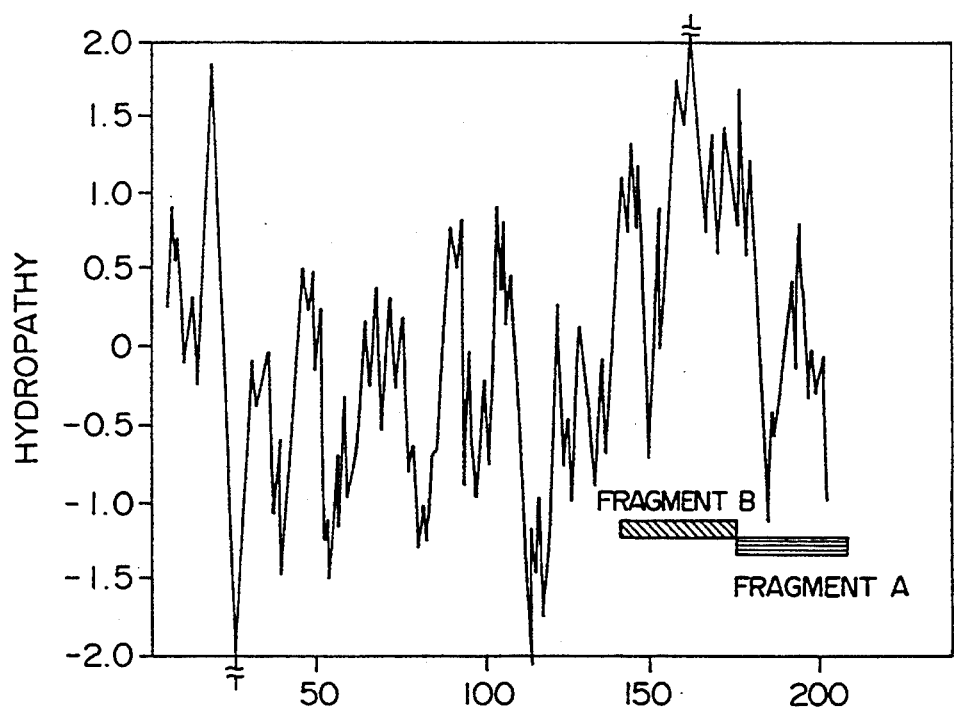
Figure 11B:
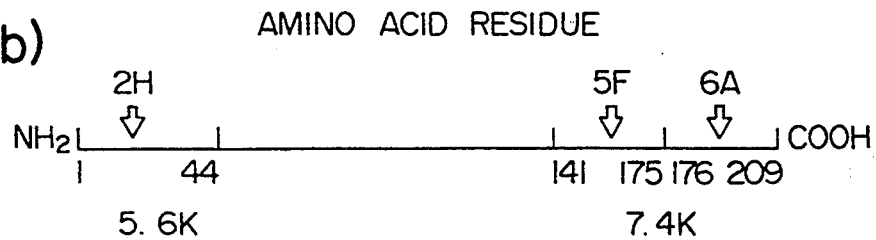

FIG. 11, (a) shows a hydropathy profile of a GST-π molecule, and FIG. 11, (b) shows the reaction sites of various monoclonal antibodies finally determined with respect to various monoclonal antibodies.

Figure 12:
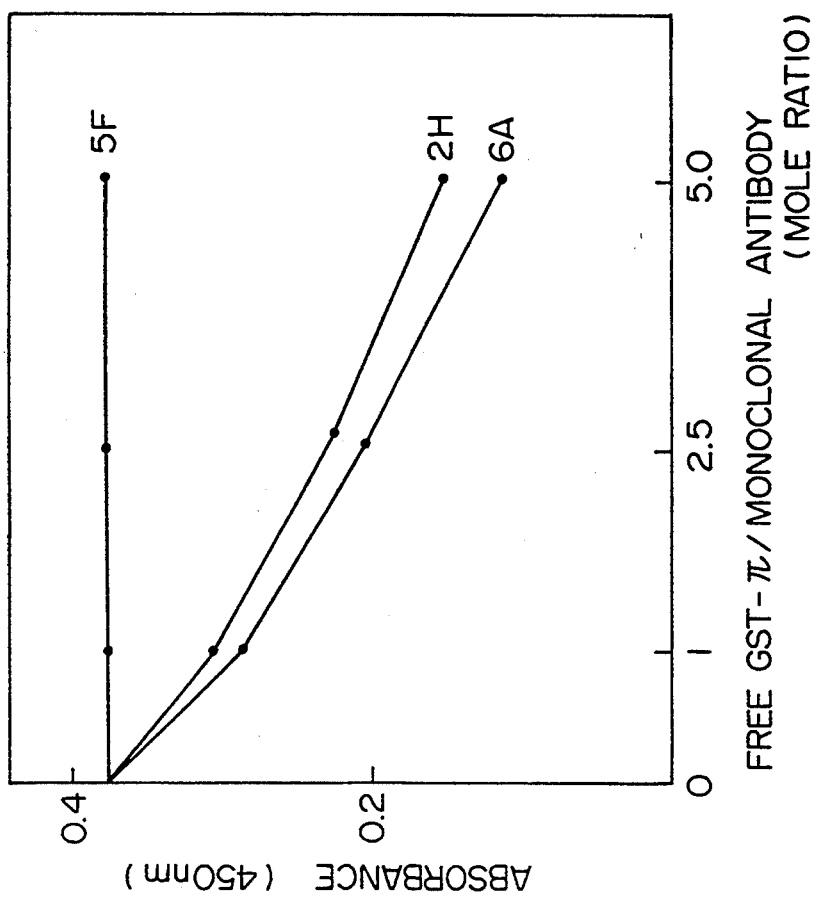

FIG. 12 shows the antigen molecule reaction specificities of monoclonal antibodies. It is seen from FIG. 12 that monoclonal antibodies 2H and 6A which recognize a liquid-phase antigen decrease in the amount of binding to a solid-phase antigen as the amount of a floating antigen is increased with respect to the solid-phase antigen. On the other hand, monoclonal antibody 5F which recognizes only a solid-phase antigen does not decrease in the amount of binding to the solid-phase antigen even when the amount of the floating antigen is increased with respect to the solid-phase antigen.

Figure 13:
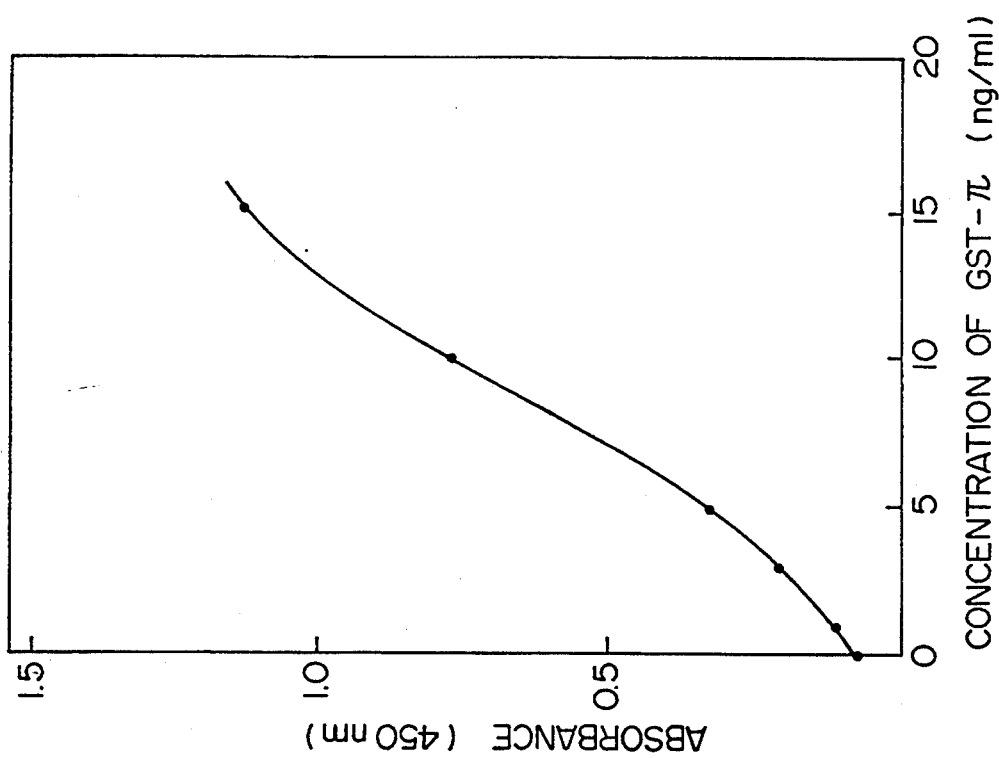

FIG. 13 is a GST-π assaying calibration curve prepared by using monoclonal antibody 2H which specifically recognizes a region of the amino acid sequence of a GST-π molecule ranging from amino acid residue Pro at the N-terminus to 44th amino acid residue Lys and monoclonal antibody 6A which specifically recognizes a region of the amino acid sequence of the same molecule ranging from 176th amino acid residue Leu to the 209th amino acid residue Gln from its N-terminus.

Figure 14B:
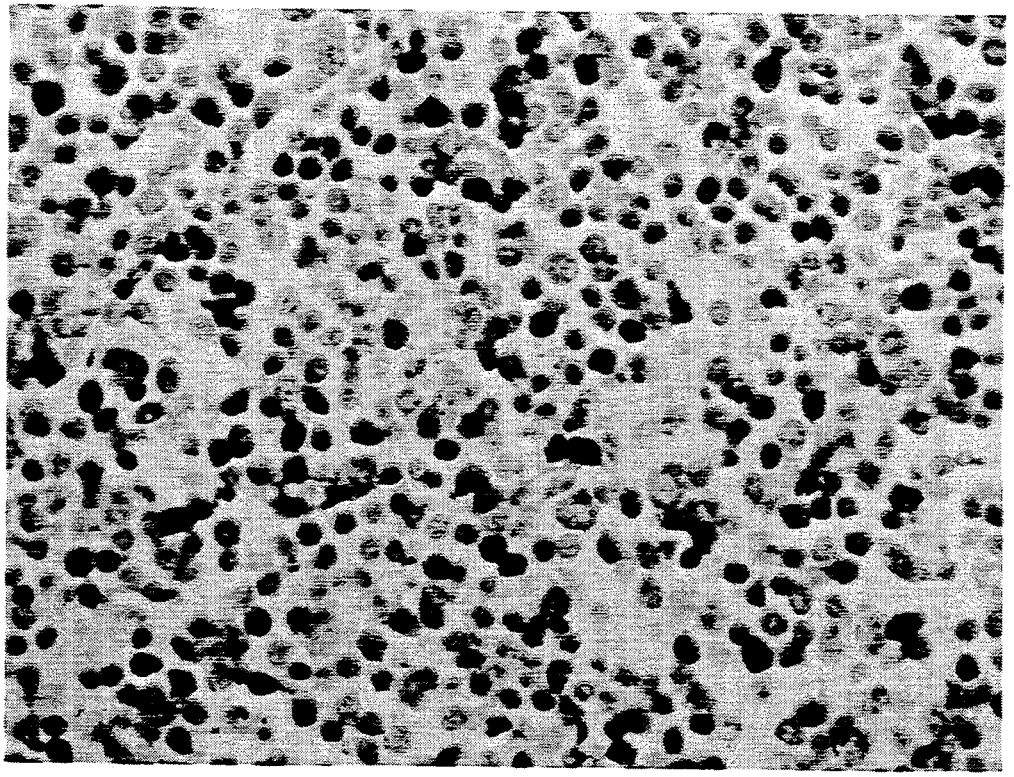
Figure 14A:
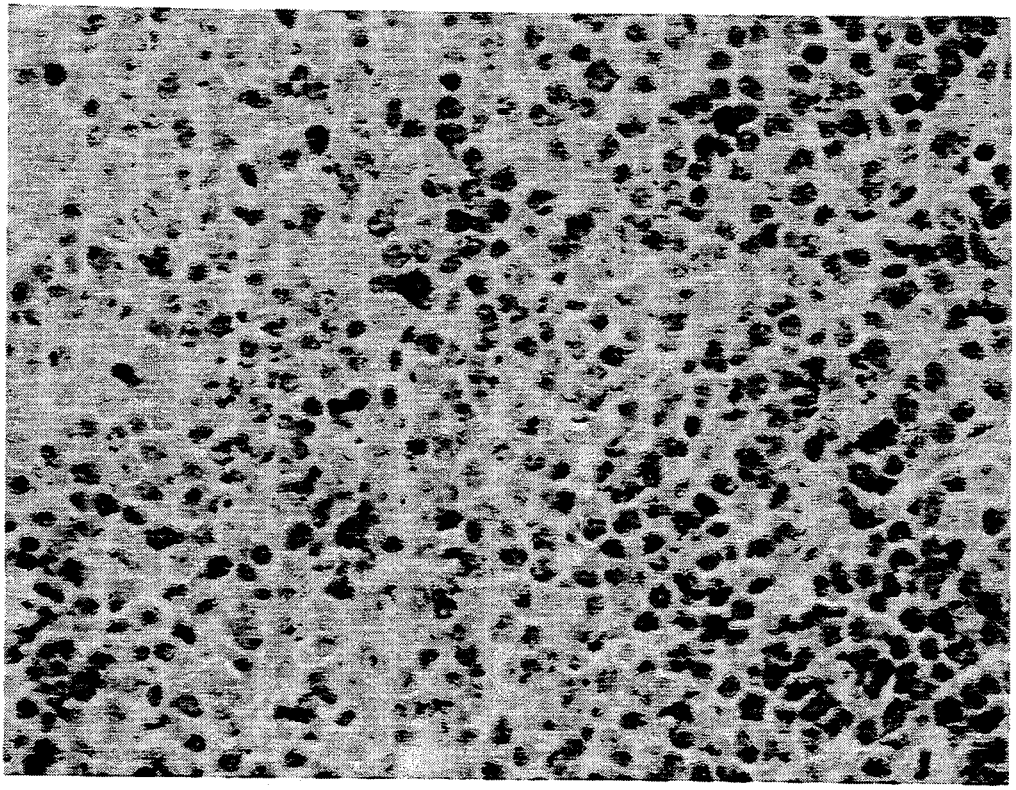

FIG. 14 shows photographs of lympho node tumor tissue from a liver cancerous patient immunologically stained by using a monoclonal antibody which specifically recognizes a region of the amino acid sequence of a GST-π molecule ranging from 14th amino acid residue Thr to the 175th amino acid residue Leu from its N-terminus, (a) being a control (after chemotherapy) and (b) showing a positive result (before chemotherapy).

Figure 15:
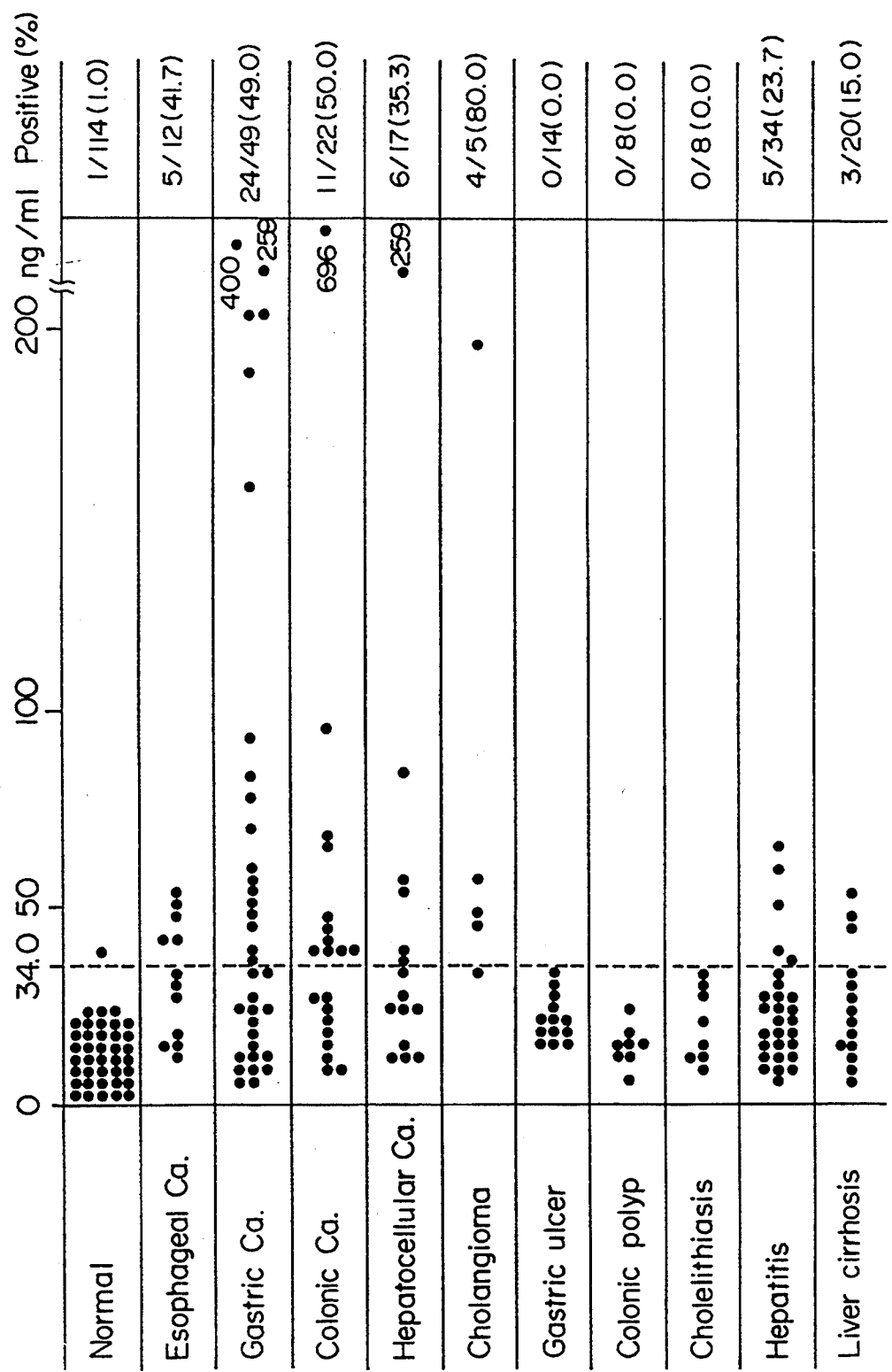

FIG. 15 shows the results of determination of human acid GST (GST-π) in clinical assay samples taken from normal subject and patients with various gastrointestinal and hematological diseases.

FIG. 16 shows the amino acid sequence of human acid GST (GST-π).

The following Examples illustrate the present invention more specifically.

In these examples, the following abbreviations are used.
BSA: bovine serum albumin PBS: phosphate-buffered saline
3% BSA/PBS: PBS containing 3% (w/v) of BSA
PVDF membrane: polyvinylidene difluoride membrane (produced by Pharmacia Co.)
HRP: horseradish peroxidase

EXAMPLE 1

Isolation and Purification of Human GST-π

Human placenta was minced in 10 mM phosphate buffer (pH 7.4) containing 0.2M sucrose, and homogenized by a homogenizer. The homogenate was centrifuged at 10,000 G and 4° C. for 30 minutes, and the supernatant was collected. The supernatant was further centrifuged at 100,000 G and 4° C. for 1 hour, and the resulting supernatant was collected. This supernatant was dialyzed against 10 mM phosphate buffer (pH 6.8). The dialyzate was passed through a carboxymthyl-filled column equilibrated with 10 nM phosphate buffer and a non-adsorbed fraction was collected. This fraction was a column filled with reduction-type glutathione-fixed Sepharose to permit adsorption of GST-π. Then, the column was washed with 10 mM phosphate buffer (pH 7.4). When the absorption intensity at 280 nm in the ultraviolet absorption spectrum of the effluent reached less than 0.02, Tris buffer (pH 8.0) containing reduction-type glutathione was passed through the column to elute the adsorbed matter. The eluate was ultrafiltered and then gel-filtered on a Sephadex G-100 (produced by Pharmacia Co.) column using 10 mM PBS (pH 7.4) to give a reaction containing human GST-π. This fraction was again concentrated by ultrafiltration, and electrofocused (pH 3.5–10) on an electrofocusing column (made by LKB Company) using sucrose for preparation of a concentration gradient and Anpholine (produced by Pharmacia Co.; pH 3.5–10) for preparation of a pH gradient to give a fraction containing purified human GST- .

(2) Preparation of an Antibody

The human GST-π extracted and collected from human placenta as above was emulsified in Freund's complete adjuvant and administered intraperitoneally to 7-week old BALB/C mice at a rate of 100 mg/mouse. Fifteen days later, the mice were additionally immunized by the same method as the first immunization. Ten days later, it was determined that the amount of an antibody increased in the blood. After a further period of 7 days, the antigen was intravenously administered to the mice as a final immunization at a rate of 100 mg/mouse.

In the meantime, myeloma cells, P3-X63-AgS-U1 had been cultured in RPMI 1640 (produced by Gibco Ltd.) containing 15% of bovine fetal serum. Three days after the final immunization, spleen cells taken out from the mice and the myeloma cells, P3-X63-AgS-U1, were fused in the presence of polyethylene glycol 4000 by the method of Oi et al. (see Selective Methods in Cellular Immunology, 1980, pp. 351–372), and added to a 96-well microplate. After the cell fusion, the medium was replaced by RPMI medium supplemented with 100 μM hypoxanthine, 0.4 μM aminopterine and 15 μM thymidine (HAT medium). During culturing in the. HAT medium, only hybridomas resulting from fusion of the spleen cells and the myeloma cells grew in 2 to 3 weeks. The antibody activity of the hybridomas in the culture broth was examined by the ELISA method described below.

(3) Antibody Screening

Human GST-π was adhered to an ELISA plate, and blocked with a mixture of 10 mM PBS (pH 7.4) and 3% (w/v) of BSA. After the blocking, 50 ml of the hybridoma culture was added to the ELISA plate and left to stand at room temperature for 2 hours. Then, the hybridoma culture was removed, and the plate was washed. Then, 100 ml of a peroxidase-labelled goat anti-mouse IgG-Fc-specific antibody (2 mg/ml) was added, and reacted at 3° C. for 1.5 hours. This enzyme-labelled antibody solution was removed, and the plate was washed. Then, 200 ml of 0.1M citrate buffer (pH 4.6) containing 0.05% of 2,2′-azinodi-[3-ethylbenzothiazolinesulfonate (6)] (ABTS) and 0.0034% of $H_2O_2$ was added to induce color formation to detect monoclonal antibodies to human GST-π.

(4) Cloning and the Preparation of Monoclonal Antibodies

The hybridoma culture producing antibodies to human GST-π was screened, and cloned by a limiting dilution method. Finally, three hybridomas each as a single clone were obtained. The hybridomas were administered to the abdominal cavities of BALB/C mice to which pristan had been administered. The hybridomas were proliferated to give ascites containing monoclonal antibodies. A 50% saturated aqueous solution of ammonium sulfate was added to the ascites to precipitate antibodies. The precipitate was dissolved in 0.1M PBS (pH 8.0), and dialyzed. The dialyzate was charged on a protein A-fixed Sepharose CL4B column (produced by Pharmacia Co.), and the antibodies were eluted with 0.2M glycine-HCl buffer (pH 3.0), neutralized and purified.

The monoclonal antibodies obtained from the three hybridomas were named 5F, 2H and 6A, respectively.

(5) Properties of the Monoclonal Antibodies

It was found by western blotting that the three monoclonal antibodies recognized GST (GST-π) derived from human fetuses. It was also found by inhibition assay comprising reacting a first biotin-labelled antibody and a second non-labelled antibody with human GST-π fixed to an ELISA plate that the amount of the biotin-labelled antibody reacted remained unchanged in a combination of any two of the three monoclonal antibodies. This shows that the three monoclonal antibodies recognized different epitopes.

These antibodies did not react with human basic GST, and hardly reacted with the serum of a normal subject.

(6) Western Blotting

An antigen specific for a monoclonal antibody was fixed by using the western blotting method in accordance with Towbing et al. (Pro. N. A. S., 76, 4350 and 4354).

First, human GST-π was subjected to SDS-PAGE. After SDS-PAGE, the protein was transferred from the slab gel to a nitrocellulose sheet using a 20% (V/V) aqueous methanol solution containing 25 mM glycine as a buffer for an electrolytic solution with a potential gradient of 7 V/cm over 2 hours. The lanes of the nitrocellulose sheet were separated from each other. One peeled sheet was subjected to protein staining with Amide Black, and the other remaining sheet was subjected to enzyme-linked immunosorbent assay by the following procedure.

The sheet was blocked with 3% (w/v) BSA/PBS, and a monoclonal antibody (2H or 5F) was added as a first antibody. A peroxidase-labelled goat anti-mouse IgG-Fc-specific antibody was added as a second antibody. The sheet was then washed and a substrate solution composed of 0.04% of 3,3′-diaminobenzidine, 0.0034% of $H_2O_2$ and 0.01M PBS was added to induce coloration. Thus, the antigen was fixed.

EXAMPLE 2

Determination of an Antigenic Determinant of Antigen (Human GST-π) to Monoclonal Antibody (Anti-Human GST-π)

(1) Digestion of human GST-π, SDS-PAGE, western blotting, separation by high-performance liquid chromatography (HPLC), and the method of preparing an anti-human GST-π polyclonal antibody were as follows:

(a) Digestion of human GST-] by CNBr

Human GST-π was digested by mixing 2.5 micrograms of human GST-π, 5 microliters of Tris-HCl (25 mM, pH 7.7), 40 micrograms of CNBr and 10 microliters of formic acid, and maintaining the mixture overnight at 25° C.

(b) Digestion of human GST-π with fixed trypsin

Human GST-π was digested by mixing 25 micrograms of GST-π), 50 microliters of 25 mM TRis-HCl (pH 7.7) and 10 microliters of a fixed trypsin suspension (20 U/microliter, Sigma Co., U.S.A.), and maintaining the mixture at 37° C. for 10 minutes.

(C) SDS-PAGE

SDS-PAGE was carried out using a 17.5% acrylamide gel containing 0.1% of SDS and a 5% acrylamide slab gel containing 0.1% of SDS. As molecular weight markers, markers for 97.4K, 66.1K, 45.0K, 31.0K, 21.5K and 14.4K were obtained from Biorad Lab., and markers for 21.5K, 12.5K and 6.5K, from Berhlinger-Mannheim. The human GST-π (2.5 micrograms) digested with CNBr and 5 micrograms of human GST-π digested with fixed trypsin were placed on one lane of the slab gel, and electrophoresed at a fixed current of 40 mA.

(d) Western blotting

After decomposition by SDS-PAGE, the protein was electrophoretically transferred from the acrylamide slab gel to the nitrocellulose membrane (250 aA, 2.5 hours) using an electric transfer device made by Biorad Lab.

After the transfer, the nitrocellulose membrane was after-coated with PBS containing 3% BSA and reacted at 37° C. for 1 hour, and then with 3% BSA containing 40 micrograms of MCA at 4° C. for 16 hours. The nitrocellulose membrane was then washed three times with PBS (T-PBS) containing 0.05% Tween 20, and reacted with a 3% BSA solution containing a peroxidase-labelled anti-mouse IgA (Capel) for 2 hours. The nitrocellulose membrane was washed four times with T-PBS, and a protein derived from human GST-π on the nitrocellulose membrane was colored using 4-chloro-1-naphthol.

(e) Separation of the trypsin-digested product of human GST-π by HPLC

All chromatography was carried out using a Toso Model. Flowing was monitored at 280 um and 210 um. One hundred micrograms of the fixed trypsin digested product of human GST-π was separated by using a linear gradient [acetonitrile 0 to 80% (160 minutes)] based on 0.1% TFA in reversed phase HPLC system on a C-18 column. The individual peaks were collected, concentrated by using a Speed Vac Concentrator and subjected to western blotting, dot blotting and a peptide sequencer of ABI Company.

(2) Reactivities of monoclonal antibodies with the CNBr-digested fragment

Figure 1:
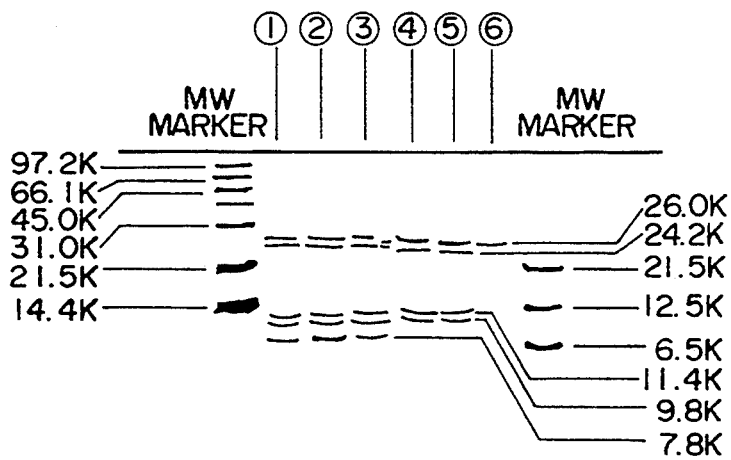
FIG. 1 is an SDS-PAGE pattern of a CNBr-cleaved fragment of a GST-$\pi$ molecule. Lane 6 shows GST-$\pi$ as a starting material. The weight ratio of cyanogen bromide to GST-$\pi$ increases as the cleavage proceeds from lane 5 to lane 1.
Figure 2:
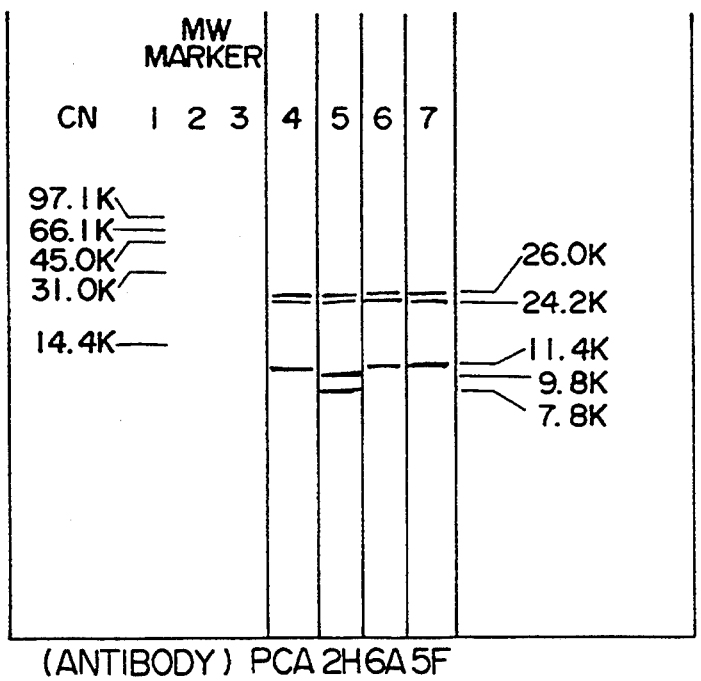
FIG. 2 is a diagram of western blotting showing the reactivities of various antibodies with a CNBr-cleaved fragment of GST-T$\pi$. The following antibodies were reacted in the individual lanes.

To determine antigenic determinants for the monoclonal antibodies, human GST-π was digested with CNBr (FIG. 1). The CNBr-digested fragment was subjected to SDS-PAGE, transferred to a nitrocellulose membrane and subjected to western blotting. The results are shown in FIG. 2. It was found from FIG. 2 that the antigenic determinants for these monoclonal antibodies are roughly of two types. Specifically, in addition to 26K (human GST-π as the material) and a 24.2K fragment, there were monoclonal antibodies 6A and 5F recognizing 11.4K and a monoclonal antibody 2H recognizing 9.8K and 7.8K.

From the total amino acid sequence of human GST-π reported by Muramatsu et al., Cancer Res., 47; 5626–5630 (1987), fragments of resulting from digestion of human GST-π with CNBr are considered to be as shown in FIG. 3. Methionine exists in the 19th and 91st places from the N-terminus. It is presumed from the foregoing that the digestion fragments are 190 residues (24.2K, 20→209), 118 residues (11.4K, 92→209), 91 residues (9.8K, 1→91) and 72 residues (7.8K, 20→91).

Accordingly, it is presumed (FIG. 4) that the monoclonal antibody 2H recognizes a region of human GST-π ranging from 1st to 91st amino acids, and monoclonal antibodies 6A and 5F and polyclonal antibody (PCA) recognize a region of human GST-π ranging from 92nd to 209th amino acids.

(3) Reactivities of monoclonal antibodies with fixed trypsin-digested fragments

Human GST-π was digested with fixed trypsin, and then subjected to SDS-PAGE (FIG. 5). Western blotting was then carried out, and the results are shown in FIG. 6.

FIG. 6 shows that the monoclonal antibody 2H recognizes a 5.6K fragment of the trypsin-digestion product, and the monoclonal antibodies 6A and 5F recognize a 7.4K fragment of the trypsin-digestion product.

Attempts were made to isolate the 5.6K fragment and the 7.4K fragment by reversed phase HPLC (Toso CCPM, TSK gel ODS-120T). Part of the resulting chromatogram is shown in FIG. 7. Peaks Nos. 37 to 43 were subjected to dot blotting, and their reactivities with the monoclonal antibodies were examined. The reaction of peak No. 40 with the monoclonal antibody 2H was determined (FIG. 8). Fraction corresponding to peak No. 40 was stretched and dried by means of a Speed Vac Concentrator, dissolved again in TFA, and applied to a peptide sequencer made by ABI Company. It was found that 20 residues from the N-terminus of this fragment have the sequence shown in FIG. 9. On comparison with the amino acid sequence of human GST-π reported by Muramatsu et al., they completely agreed with the 20 residues from the N-terminus of human GST-π.

From the fact that Lys exists in the 44th residue from the N-terminus of human GST-π, it was determined that the 5.6K fragment is a fragment ranging from the N-terminus to the 44th residue of human GST-π, and the monoclonal antibody 2H recognizes this fragment. The recognition of the fragment on the N-terminus side by the monoclonal antibody 2H is also supported by the experimental fact that the monoclonal antibody recognizes a CNBr-digested fragment of human GST-π consisting of 1st (Pro) to 91st (Met) amino acids.

Separation of the 7.4K fragment was examined by using reversed phase HPLC. But suitable isolation conditions could not be found and this fragment could not be isolated. Thus, its isolation by using a slab gel was examined. Specifically, the trypsin digested product of human GST-π was placed on a slab gel (18×8 cm) at a rate of 200 micrograms per lane, and subjected to SDS-PAGE. After electrophoresis, the protein was transferred (90 V, 30-0 mA, 30 minutes, room temperature) to a PVDF membrane (produced by Pharmacia Co.) and stained with Coumasie Blue. The desired band was cut off and directly applied to a peptide sequencer (made by ABI Company). It was found that its N-terminus amino acid sequence is $^1$Thr-Phe-Ile-Val-Gly.

It was compared with the human GST-π amino acid sequence reported by Muramatsu et al., and it was found that the sequence of 5 residues from $^{141}$Lys to $^{145}$Gly agreed completely with the sequence of human GST-π. It was concluded therefore that the 7.4K fragment consisted of $^{141}$Thr to $^{209}$Gln. It was found that the monoclonal antibodies 6A and 5F recognize a fragment of $^{141}$Thr-Gln on the C-terminus side. This is also supported by the experimental fact that the monoclonal antibodies 5A and 5F a fragment which results from digestion of human GST-π with CNBr and consists of the 92nd to 209th amino acid residues of human GST-π.

(4) Reactivities of the monoclonal antibodies with synthetic peptides

In order to determine the reactivities of the monoclonal antibodies 6A and 5F, a peptide composed of 69 residues, $^{141}$Thr-$^{209}$Gln, on the C-terminus side was synthesized as two fragments, i.e. fragment A ($^{176}$Leu-$^{209}$Gln) and fragment B ($^{141}$Thr-$^{175}$Leu). The synthesized peptides were purified, and spoted on a nitrocellulose membrane in an amount of 100 ng and 10 ng, respectively. Dot blotting was carried out using the monoclonal antibodies. As shown in FIG. 10, it was found that the monoclonal antibody 6A reacted specifically with fragment A, and the monoclonal antibody 5F, with fragment B.

The following conclusion can be drawn from the above results.

(1) The monoclonal antibody 6A reacts with the epitope of the $^{176}$Leu-$^{209}$Gln on the C-terminus side.
(2) The monoclonal antibody 5F reacts with the epitope of the $^{141}$Thr-$^{175}$Leu fragment.
(3) The monoclonal antibody 2H reacts with the epitope of the $^1$Pro-$^{44}$Lys fragment on the N-terminus side.

EXAMPLE 3

Reaction Specificity Between a Monoclonal Antibody and a Human GST-π Molecule

A PBS solution of human GST-π in a concentration of 1 microgram/ml was added at a rate of 50 microliters/well to fix the antigen (human GST-π). The plate was then after-coated with 1% PBS. Then, 50 microliters of a solution of each of various monoclonal antibodies and 50 microliters of 1% BSA/PBS containing an antigen in an amount 1, 2.5 or 5.0 times the amount of the solid-phase antigen were added in each well and reacted at room temperature for 1 hour. After washing, a dilute solution of anti-mouse IgG/HRP complex was added. The plate was washed and tetramethylbenzimine was added to induce coloration. The results are shown in FIG. 12.

The results show that the monoclonal antibodies are classified into two groups having different reactivities, namely the monoclonal antibodies 6A and 2H showing high reactivity with the antigen liberated in the liquid phase, and the monoclonal antibody 5F showing no reactivity with the antigen liberated in the liquid phase.

EXAMPLE 4

Enzyme-Linked Immunosorbent Assay of Human GST-$\pi$

One bead to which the monoclonal antibody 2H capable of recognizing a region of the amino acid sequence of a human placenta-derived GST-$\pi$ molecule ranging from the N-terminus to the 44th amino acid, 200 microliters of 0.5% BSA/PBS (pH 7.4) solution containing 10 to 15 ng/ml of purified human GST-$\pi$, and 200 microliters of a 0.5% BSA/PBS solution (pH 7.4) containing HRP-labelled monoclonal antibody 6A capable of recognizing a region of the amino acid sequence of human GST- ranging from 176th residue to the 209th residue from the N-terminus were added to a test tube and incubated at 37° C. for 4 hours.

The solution in the test tube was removed by sucking, and the test tube was washed with PBS. Then, 0.4 ml of a 0.1M phosphate/citrate buffer (pH 4.0) containing 0.02% of 3,3',5,5'-tetramethylbenzidinehydrochloride and 0.005% of $H_2O_2$ was added to the test tube and incubated at 37° C. for 30 minutes. Then, 1 ml of a 1N aqueous solution of sulfuric acid was added as a reaction stopper to stop the enzyme reaction.

The absorbance of the solution at 450 nm was measured by using a spectrophotometer, and plotted against the concentration of a standard substance to give a calibration curve for determination of human placenta-derived GST (see FIG. 13).

EXAMPLE 5

Preparation of an Anti-Human GST-$\pi$ Polyclonal Antibody

Human GST-$\pi$ (200 micrograms) was mixed with Freund's complete adjuvant, and the mixture was subcutaneously injected at the back of a rabbit. Two weeks later, 100 micrograms of human GST-$\pi$ was mixed with 1 ml of Freund's incomplete adjuvant, and the mixture was likewise administered subcutaneously. The booster was applied three times in total, and ten days after the final immunization, the whole blood was drawn from the animal.

The antibody was purified by using protein A-fixed Sepharose CL4B. One gram of the protein A-fixed Sepharose CL4B (produced by Pharmacia Co.) was swollen with PBS, and packed into a column. Antiserum (3 cc) was mixed with 3 cc of 0.1M phosphate buffer (pH 8.5), and the mixture was applied to the resulting column. The column was then well washed with 0.1M phosphate buffer. Finally, the antibody bound to the protein A column was eluted with 0.1M citrate buffer. The eluted antibody solution was dialyzed against PBS to give a purified antibody.

EXAMPLE 6

Comparison of the Sensitivities of Various Methods of Determining GST-$\pi$ (1) Fixing and labelling of the polyclonal antibody and monoclonal antibodies 6A, 5F and 2H were carried out by the following procedures.

(a) Preparation of antibody-fixed beads

Polystyrene beads (diameter 6 mm) were well washed, and left to stand for one day at 4° C. in a PBS (pH 7.4) solution containing each of the various anti-human GST-$\pi$ antibodies in a concentration of 20 micrograms/ml. The beads were then washed with PBS, and after-coated by leaving it to stand for one day at 4° C. in a 0.5% aqueous solution of BSA to give anti-human GST-$\pi$ antibody-fixed beads.

(b) Preparation of HRP-labelled antibody

Fifty milliliters of a dimethylformamide solution of N-(m-maleimidebenzoic acid)-N-succinimide ester (MBS) in a concentration of 10 mg/ml was added to a 1.0 mg/ml PBS solution of the anti-human GST-$\pi$ antibody, and reacted at 25° C. for 20 minutes. The reaction product was gel-filtered with 0.1M phosphate buffer (pH 6.0) on a column filled with Sephadex G-25 to separate the resulting antibody from the unreacted MBS.

An ethanol solution of N-succinimidyl-3-(2-pyridyl-thio)propionate (SPDP) in a concentration of 10 mg/ml was added to a PBS solution of HRP in a concentration of 1.0 mg/ml, and reacted at 25° C. for 30 minutes. The reaction product was then purified by gel filtration with 0.1M acetate buffer (pH 4.5) on a column filled with Sephadex G-25. Fractions containing HRP having the pyridyl disulfide group introduced thereinto were collected and diluted to about 10-fold under ice cooling in a collodion bag. Then, 1 ml of 0.1M acetate buffer (pH 4.5) containing 0.85% of NaCl and 0.1M dithiothreitol was added, and the mixture was stirred at 25° C. for 30 minutes to reduce the pyridyl disulfide group introduced into the HRP molecule. The product was then gel-filtered on a Sephadex G-25 column to give a fraction containing the thiol group introduced thereinto.

The maleimidized antibody and the thiol-introduced HRP were mixed and concentrated to a protein concentration of 4 mg/ml under ice cooling. The concentrate was left to stand for one day at 4° C., and gel-filtered on a column filled with an ultrogel AcA44 (LKB Company) to give a HRP-labelled anti-human GST-$\pi$ antibody.

(2) Determination of human GST-$\pi$ by a simultaneous sandwich enzyme immunoassay (using a polyclonal antibody as a labelled antibody)

One bead to which each of various antibodies (polyclonal antibody and monoclonal antibodies 6A, 5F and 2H), 200 microliters of a 0.5% BSA/PBS solution (pH 7.4) containing 0 to 15 ng/ml of purified human GST-$\pi$ (standard substance) and 200 microliters of a 0.5% BSA/PBS solution containing HRP-labelled rabbit anti-GST-$\pi$ polyclonal antibody were added to a test tube, and incubated at 37° C. for 2 hours. The solution in the test tube was removed by suction, and the test tube was washed with PBS. Then, 0.4 ml of 0.1M phosphate/citrate buffer (pH 4.0) containing 0.02% of 3,3',5,5'-tetramethylbenzidinehydrochloride and 0,005% of $H_2O_2$ was added to the test tube and incubated at 37° C. for 30 minutes. Then, 1 ml of a 1N aqueous solution of sulfuric acid was added as a reaction stopper to stop the enzyme reaction.

The absorbance at 450 nm of the resulting solution was measured by a spectrophotometer and piotted against the concentration (0 and 15 ng/ml) of the standard Substance, and the N/S ratio (ODAg=O/OD Ag=15 ng/ml) according to various solid-phase antibody combinations were calculated. The results are shown in Table 1.

TABLE 1

| Solid-phase antibody | OD$_{450}$ (GST-π; 0 ng/ml) | OD$_{450}$ (GST-π; 15 ng/ml) | N/S ratio (%) |
|---|---|---|---|
| Polyclonal antibody | 0.182 | 0.825 | 22.1 |
| Monoclonal antibody 6A | 0.063 | 0.728 | 8.7 |
| Monoclonal antibody 5F | 0.081 | 0.145 | 55.8 |
| Monoclonal antibody 2H | 0.056 | 0.613 | 9.1 |

It is seen from Table 1 that with an assay system composed of the HRP-labelled rabbit anti-human GST-π polyclonal antibody and the monoclonal solid-phase antibody 6A or 2H, the N/S ratio is low and the absorbance at a human GST-π concentration of 0 ng/ml is maintained low, and the absorbance at 15 ng/ml is sufficiently high. Thus, this assay system has high sensitivity.

(3) Determination of human GST-π by simultaneous sandwich enzyme immunoassay (using a polyclonal antibody as the solid-phase antibody)

The experiment in section (2) above as followed using various enzyme-labelled antibodies (polyclonal antibody and monoclonal antibodies 6A, 5F and 2H) and polyclonal antibody-fixed beads.

The results are shown in Table 2. It is seen from Table 2 that an assay system composed of the solid-phase polyclonal antibody and the enzyme-labelled monoclonal antibody 6A or 2H is a good assay system with a low N/S ratio.

TABLE 2

| Solid-phase antibody | OD$_{450}$ (GST-π; 0 ng/ml) | OD$_{450}$ (GST-π; 15 ng/ml) | N/S ratio (%) |
|---|---|---|---|
| Polyclonal antibody | 0.215 | 0.662 | 32.8 |
| Monoclonal antibody 6A | 0.043 | 0.813 | 5.3 |
| Monoclonal antibody 5F | 0.034 | 0.096 | 35.4 |
| Monoclonal antibody 2H | 0.052 | 0.729 | 7.1 |

(4) Absorption test using fixed fragment A [$^{176}$Leu-$^{209}$Gln] of a rabbit polyclonal antibody This experiment was carried out in order to determine how much antibody having an epitope for the above fragment A is contained in the above rabbit human GST-π polyclonal antibody.

The fragment A (20 mg) was dissolved in 1 ml of 0.1M carbonate buffer (pH 9.0), and reacted overnight at 4° C. with 1 ml of CNBr-activated Sepharose 4B (Pharmacia Co.). The fragment A-fixed Sepharose 4B was washed with 3M KSCN and filled in a column, and reacted with 2 ml of rabbit GST-π polyclonal antibody. The column was washed with 100 ml of PBS, and eluted with 3M KSCN. The absorbance at 280 nm of the eluate was 0.016.

For comparison, the same absorption experiment was carried out using Sepharose 4B to which 1 mg of human GST-π was fixed. The absorbance at 280 nm of 5 ml of the resulting eluate was 0.352. The former value, 0.016 (11.5 micrograms/ml) corresponded to 4.6% of the total anti-GST-π antibody value, 0.352 (251 micrograms/ml).

The above results show that the rabbit anti-human GST-π polyclonal antibody does not have an epitope in common with the monoclonal antibody (see Example 1) recognizing the sequence from the N-terminus to the 44th residue from the N-terminus of the human GST-π molecule, nor with the monoclonal antibody recognizing the sequence from the 176th residue to the 209th residue from the N-terminus [Example 6, (4)]. It could be ascertained that an assay system composed of the polyclonal antibody and the monoclonal antibody recognizing the sequence from the N-terminus to the 44th residue from the N-terminus and having a different epitope from the polyclonal antibody and an assay system composed of the polyclonal antibody and the monoclonal antibody recognizing the sequence from the 176th residue to the 209th residue from the N-terminus have high sensitivity with a low N/S ratio.

This can be substantiated from the fact that a combination of polyclonal antibodies having the same epitope as used in the comparative experiment could give an assay system of high sensitivity because a nonspecific reaction was strong, and that a combination of a polyclonal antibody and the monoclonal antibody 5F ($^{141}$Thr-$^{175}$Leu was its antigenic determinant) which might have a common antigenic determinant could not give an assay system of high sensitivity because of a specific reaction.

EXAMPLE 7

Determination of GST-π Using an HRP-Labelled Monoclonal Antibody F(ab')$_2$ (1) Labelling of monoclonal antibody F(ab')$_2$ with HRP One hundred microliters of 1M acetate buffer (pH 3.7) and a solution of 40 micrograms of pepsin in 30 microliters of the same buffer as above were added to a 3.0 mg/ml PBS solution of monoclonal antibody 6A, and reacted at 37° C. for 3 hours. After the reaction, the reaction mixture was separated on a PBS-equilibrated Sephadex G-25 column (2 cm in diameter, 45 cm in length) to collect F(ab')$_2$. HRP-labelled monoclonal antibody 6A-F(ab')$_2$ was prepared as in Example 2, (1), (b).

(2) Determination of GST-π by simultaneous sandwich enzyme immunoassay

Purified GST-π (standard substance) in a concentration of 0 to 15 ng/ml was determined by immunoassay in accordance with Example 2, (2) using beads to which rabbit human GST-π polyclonal antibody was fixed and HRP-labelled monoclonal antibody 6A-F(ab')$_2$. For comparison, the assay was conducted using HRP-labelled monoclonal antibody 6A-IgG. The results are shown in Table 3.

TABLE 3

| HRP-labelled antibody | Antigen concentration (mg/ml) | Average OD (X) | Standard deviation (SD) | X̄ + 2SD | X̄ − 2SD |
|---|---|---|---|---|---|
| Monoclonal antibody 6A-IgG | 0 | 0.041 | 0.0014 | 0.0438 | |
| | 0.5 | 0.055 | 0.0032 | | 0.0486 |
| | 1.0 | 0.070 | 0.0048 | | 0.0604 |
| | 2.0 | 0.094 | 0.0067 | | 0.0806 |
| Monoclonal antibody 6 6A-F(ab')$_2$ | 0 | 0.101 | 0.0040 | 0.1090 | |
| | 0.5 | 0.108 | 0.0051 | | 0.0978 |
| | 1.0 | 0.1.14 | 0.0063 | | 0.1014 |
| | 2.0 | 0.138 | 0.0070 | | 0.1240 |

As shown in Table 3, the HRP-labelled monoclonal antibody 6A-F(ab')$_2$ showed three to four times as high selectivity as monoclonal antibody 6A-IgG.

EXAMPLE 8

Determination of GST-$\pi$ Using Rabbit HRP-Labelled Human GST-$\pi$ Polyclonal Antibody Fab'

(1) Labelling of rabbit human GST-$\pi$ polyclonal antibody Fab' with HRP

One hundred microliters of 1M acetate buffer (pH 4.2) and a solution of 40 micrograms of pepsin in 20 microliters of the same buffer as above were added to a 2 mg/ml PBS solution of rabbit anti-human GST-$\pi$ polyclonal antibody, and reacted at 30° C. for 16 hours. After the reaction, the reaction mixture was separated on a Sephadex G-25 column (2 cm in diameter, 45 cm in length) equilibrated with 0.1M phosphate buffer (pH 6.0) containing 5 mM EDTA to collect F(ab')$_2$. F(ab')$_2$ was reduced with mercaptoethylamine, and subjected to gel filtration and HPLC to isolate purified Fab'.

6A-F(ab')HRP was treated with MBS to prepare maleimidized HRP. The Fab' was mixed with maleimidized HRP, and the mixture was concentrated by using Filtron (ultrafiltration unit) and reacted. The reaction was carried out overnight at 4° C. HRP-labelled monoclonal antibody 6A was isolated and purified by using Toso G3000SW.

(2) Determination of GST-$\pi$ by simultaneous sandwich enzyme immunoassay

Purified human GST-$\pi$ (standard substance) in a concentration of 0 to 15 ng/ml was determined by immunoassay in accordance with Example 2, (2) using beads to which monoclonal antibody 6A was fixed and HRP-labelled polyclonal antibody Fab'. For comparison, the assay was conducted using HRP-labelled polyclonal antibody IgG. The results are shown in Table 4.

TABLE 4

| HRP-labelled antibody | Antigen concentration (mg/ml) | Average OD (X) | Standard deviation (SD) | $\overline{X}$ + 2SD | $\overline{X}$ − 2SD |
|---|---|---|---|---|---|
| Polyclonal antibody IgG | 0 | 0.056 | 0.004 | 0.064 | — |
| | 0.5 | 0.072 | 0.003 | — | 0.064 |
| | 1.0 | 0.087 | 0.007 | — | 0.073 |
| | 2.0 | 0.107 | 0.005 | — | 0.097 |
| Polyclonal antibody Fab' | 0 | 0.103 | 0.004 | 0.011 | — |
| | 0.5 | 0.107 | 0.007 | — | 0.093 |
| | 1.0 | 0.115 | 0.010 | — | 0.095 |
| | 2.0 | 0.148 | 0.012 | — | 0.124 |

As shown in Table 4, the HRP-labelled rabbit anti-human GST-$\pi$ polyclonal antibody Fab' showed 8 to 10 times as high sensitivity as IgG.

EXAMPLE 9

Staining of Cancer Cell Tissues

A liver cancer tissue was taken and fixed to paraffin, and then an ultrathin slice was prepared. The slice was treated with 0.1% trypsin at 37° C. for 30 minutes. To remove intrinsic peroxidase, the slice was then reacted with a methanol solution containing hydrogen peroxide (98 ml methanol/2 ml 30% hydrogen peroxide) at room temperature for 30 minutes. The reacted slice was washed with PBS and reacted with monoclonal antibody-5F (diluted to 1 microgram/ml) at room temperature for 30 minutes. The slice was then reacted with peroxidase-labelled anti-mouse IgG (diluted to 1000-fold) at room temperature for 30 minutes. After washing with PBS, the peroxidase was colored with aminobenzene to stain the tissue. The photograph of the stained tissue is shown in FIG. 14, (b) of the accompanying drawings. For comparison, a liver tissue of a normal subject was treated as above, and its photograph is shown in FIG. 14, (a). A comparison of the photographs (a) and (b) led to the determination of the presence of human acid GST in the liver cancer cells.

EXAMPLE 10

Determination of Human Acid GST (GST-$\pi$) in Clinical Samples

Serum samples were taken from a normal subject and patients with various gastrointestinal and hematological diseases. Each of the samples (50 microliters) was put in a test tube, and diluted with 150 microliters of a PBS solution (pH 7.4) containing 0.5% BAS. One bead to which rabbit anti-human placenta-derived acid GST polyclonal antibody was fixed and 200 microliters of a PBS solution (PH 7.4) containing HRP-labelled monoclonal antibody 6A 0.5% BSA were added to the test tube, and the entire mixture was incubated at 37° C. for 4 hours. The product was then subjected to washing, enzyme reaction and stopping of the reaction by the same operation as in the preparation of the calibration curve described hereinabove. Then, the absorption intensity at 450 nm of the product was measured by a spectral photometer, and the concentration of the product was determined from the calibration curve.

The results are shown in FIG. 15. The results show that the concentration of acid GST (GST-$\pi$) in the serum of the normal subject is 11.2±11.8 ng/ml, and the cut off value was 34.0 ng/ml. The amounts of acid GST in the serum samples of the patients with various diseases are tabulated below.

| Disease | Content of human acid GST (ng/ml) | Proportion above the cut off value (%) |
|---|---|---|
| Asophagal ca. | 27.5 ± 1.8 | 41.7 |
| Gastric ca. | 34.7 ± 2.6 | 49.0 |
| Colonic ca. | 29.5 ± 2.7 | 52.0 |
| Hepatocellar ca. | 26.9 ± 2.3 | 35.3 |
| Gastic ulcer | 18.7 ± 1.9 | 0.0 |
| Colonic polyp | 16.2 ± 1.4 | 0.0 |
| Cholelithiasis | 14.8 ± 1.5 | 0.0 |
| Hepatitis | 15.5 ± 2.1 | 23.5 |
| Liver dirrhosis | 16.2 ± 2.0 | 15.0 |

The results given in the above table show that there is an evident significant difference between the human acid GST content of the normal subject and that of a patient with cancer at a digestive organ, and the proportion above the cut off value is considerably higher in the cancer patient. It is also seen that in patients with other diseases of digestive organs, there is hardly any difference in the amount of human acid GST between the patient and the normal subject.

We claim:

1. A method of immunologically determining human acid glutathione S-transferase in a human assay sample, which comprises bringing the assay sample into contact with a first antibody bound to an insoluble solid carrier and a labelled second antibody, either the first or second antibody being a polyclonal antibody capable of binding to human acid glutathione S-transferase or an Fab, Fab' or F(ab')$_2$ fragment of the polyclonal antibody, and the other antibody being a monoclonal antibody capable of specifically binding to human acid glutathione S-transferase or an Fab, Fab' or F(ab,)$_2$ fragment of the monoclonal antibody, wherein said monoclonal antibody is a monoclonal antibody 6A produced by hybridoma FERM BP-3023.

2. A method of diagnosing cancer in a human digestive organ, which comprises
(i) using a first antibody bound to an insoluble solid carrier and a labelled second antibody, either the first or second antibody being a polyclonal antibody capable of binding to human acid glutathione S-transferase or an Fab, Fab' or F(ab')$_2$ fragment of the polyclonal antibody, and the other antibody being a monoclonal antibody capable of specifically binding to human acid glutathione S-transferase or an Fab, Fab' or F(ab')$_2$ fragment of the monoclonal antibody,
(ii) bringing a human assay sample into contact with the first and second antibodies,
(iii) determining the amount of human acid glutathione S-transferase contained in the sample, and
(iv) diagnosing the onset of cancer in a human digestive organ, the state of its progress or its regression on the basis of the determined amount of human acid glutathione S-transferase,
wherein said monoclonal antibody is a monoclonal antibody 6A produced by hybridoma FERM BP-3023.

3. The method of claim 1 or 2 in which the first antibody is a polyclonal antibody capable of binding to human placenta-derived glutathione S-transferase or an Fab, Fab' or F(ab')$_2$ fragment thereof, and the second antibody is a monoclonal antibody capable of specifically binding to human placenta-derived glutathione S-transferase.

4. The method of claim 1 or 2 in which the first antibody is a monoclonal antibody capable of specifically binding to human placenta-derived glutathione S-transferase or an Fab, Fab' or F(ab')$_2$ fragment thereof, and the second antibody is a polyclonal antibody capable of binding to human placenta-derived glutathione S-transferase.

5. The method of any one of claims 1 or 2 in which the polyclonal antibody binds to a region of the amino acid sequence of a human placenta-derived glutathione S-transferase molecule which ranges from the 92nd amino acid residue Val to the 209th (C-terminus) amino acid residue Gln from the N-terminus.

6. The method of claim 3 in which the polyclonal antibody binds to a region of the amino acid sequence of a human placenta-derived glutathione S-transferase molecule which ranges from the 92nd amino acid residue Val to the 209th (C-terminus) amino acid residue Gln from the N-terminus.

7. The method of claim 4 in which the polyclonal antibody binds to a region of the amino acid sequence of a human placenta-derived glutathione S-transferase molecule which ranges from the 92nd amino acid residue Val to the 209th (C-terminus) amino acid residue Gln from the N-terminus.

8. The method of any one of claims 1 or 2 in which the human assay sample is a human serum or plasma sample.

9. The method of claim 3 in which the human assay sample is a human serum or plasma sample.

10. The method of claim 4 in which the human assay sample is a human serum or plasma sample.

11. The method of any one of claims 1 or 2 in which the immune reaction is carried out in the presence of a protein having an average molecular weight of 16,000 to 50,000 and an isoelectric point of 1.0 to 5.0 or a mixture containing the protein as an antigen-antibody reaction regulating agent, the final concentration of the antigen-antibody reaction regulating agent being adjusted to 0.02 to 0.9% by weight.

12. The method of claim 3 in which the immune reaction is carried out in the presence of a protein having an average molecular weight of 16,000 to 50,000 and an isoelectric point of 1.0 to 5.0 or a mixture containing the protein as an antigen-antibody reaction regulating agent, the final concentration of the antigen-antibody reaction regulating agent being adjusted to 0.02 to 0.9% by weight.

13. The method of claim 4 in which the immune reaction is carried out in the presence of a protein having an average molecular weight of 16,000 to 50,000 and an isoelectric point of 1.0 to 5.0 or a mixture containing the protein as an antigen-antibody reaction regulating agent, the final concentration of the antigen-antibody reaction regulating agent being adjusted to 0.02 to 0.9% by weight.

14. The method of claim 11 in which the antigen-antibody reaction regulating agent is skimmed milk.

15. The method of claim 12 in which the antigen-antibody reaction regulating agent is skimmed milk.

16. The method of claim 13 in which the antigen-antibody reaction regulating agent is skimmed milk.

17. A reagent system for immunological determination of human acid glutathione S-transferase in a human assay sample, comprising a first antibody bound to an insoluble solid carrier and a labelled second antibody, either the first or second antibody being a polyclonal antibody capable of binding to human placenta-derived gluthathione S-transferase or an Fab, Fab' or F(ab')$_2$ fragment of the polyclonal antibody, and the other antibody being a monoclonal antibody capable of specifically binding to human placenta-derived glutathione S-transferase or an Fab, Fab' or F(ab')$_2$ fragment of the monoclonal antibody,
wherein said monoclonal antibody is a monoclonal antibody 6A produced by hybridoma FERM BP-3023.

18. A kit for immunological determination of human acid glutathione S-transferase in a human assay sample, comprising (a) a first antibody bound to an insoluble solid carrier, (b) a labelled second antibody, either the first or second antibody being a polyclonal antibody capable of binding to human placenta-derived glutathione S-transferase or an Fab, Fab' or F(ab')$_2$ fragment of the polyclonal antibody, and the other antibody being a monoclonal antibody capable of specifically binding to human placenta-derived glutathione S-transferase or an Fab, Fab' or F(ab')$_2$ fragment of the monoclonal antibody, (c) a dissolving agent, (d) a washing agent, and when an enzyme-labelled antibody is used, (e) a substrate for measuring the enzyme activity and a reaction stopper therefor,
wherein said monoclonal antibody is a monoclonal antibody 6A produced by the hybridoma FERM BP-3023.

19. The system of claim 17 or the kit of claim 18 in which the first antibody is a polyclonal antibody capable of binding to human acid glutathione S-transferase or an Fab, Fab' or F(ab')$_2$ fragment thereof, and the second antibody is a monoclonal antibody capable of specifically binding to human acid glutathione S-transferase.

20. The system of claim 17 or the kit of claim 18 in which the first antibody is a monoclonal antibody capable of specifically binding to human acid glutathione S-transferase or an Fab, Fab' or F(ab')$_2$ thereof, and the second antibody is a polyclonal antibody capable of binding to human acid glutathione S-transferase or an Fab, Fab' or F(ab')$_2$ fragment thereof.

21. The system of claim 17 or the kit of claim 18 in which the polyclonal antibody binds to a region of the amino acid sequence of a glutathione S-transferase molecule derived from human placenta which ranges from the 92nd amino acid residue Val to the 209th (C-terminus) amino acid residue Gln from the N-terminus.

* * * * *